(12) United States Patent
Tasker et al.

(10) Patent No.: US 7,308,334 B2
(45) Date of Patent: *Dec. 11, 2007

(54) GRAPHICAL AUTOMATED MACHINE CONTROL AND METROLOGY

(75) Inventors: David J. Tasker, Hillsboro, OR (US); Henri J. Lezec, Strasbourg (FR); David A. Head, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/115,751

(22) Filed: Apr. 27, 2005

(65) Prior Publication Data

US 2005/0188309 A1    Aug. 25, 2005

Related U.S. Application Data

(63) Continuation of application No. 10/227,619, filed on Aug. 23, 2002, now Pat. No. 6,889,113.

(60) Provisional application No. 60/314,687, filed on Aug. 23, 2001.

(51) Int. Cl.
*G06F 19/00* (2006.01)
(52) U.S. Cl. .................... 700/180; 700/182
(58) Field of Classification Search ............. 700/180, 700/166, 182, 121
See application file for complete search history.

(56) References Cited

U.S. PATENT DOCUMENTS

| | | | |
|---|---|---|---|
| 3,877,019 A | 4/1975 | Auerbach et al. | |
| 5,163,006 A | 11/1992 | Deziel | |
| 5,815,154 A | 9/1998 | Hirschtick et al. | |
| 5,926,176 A | 7/1999 | McMillan et al. | |
| 5,970,243 A | 10/1999 | Klein et al. | |
| 6,058,333 A | 5/2000 | Klein et al. | |
| 6,064,386 A | 5/2000 | Felser et al. | |
| 6,065,858 A | 5/2000 | Yamaguchi et al. | |
| 6,118,448 A | 9/2000 | McMillan et al. | |
| 6,191,850 B1 | 2/2001 | Chiang | |
| 6,219,055 B1 | 4/2001 | Bhargava et al. | |
| 6,232,985 B1 | 5/2001 | Chase et al. | |
| 6,798,515 B1 | 9/2004 | Bachelder et al. | |
| 6,868,175 B1 * | 3/2005 | Yamamoto et al. | 382/145 |
| 6,889,113 B2 | 5/2005 | Tasker et al. | |
| 2002/0125905 A1 * | 9/2002 | Borden et al. | 324/765 |
| 2003/0223066 A1 | 12/2003 | Lee et al. | |

* cited by examiner

*Primary Examiner*—Zoila Cabrera
(74) *Attorney, Agent, or Firm*—Scheinberg & Griner, LLP; Michael O. Scheinberg; David Griner

(57) ABSTRACT

A graphical programming system allows a user to place geometric shapes onto a scaled image, the shape having associated behavior that operates on the image or on the object of which the image is formed. In a preferred embodiment, the shapes are objects in the Visio program by Microsoft Corporation. The shapes are dragged from a stencil onto an image provided by ion beam or electron microscope image. The shape invokes software or hardware to locate and measure features on the image or to perform operations, such as ion beam milling, on the object that is imaged.

9 Claims, 18 Drawing Sheets ced by those skilled in the art that the conception and
GRAPHICAL AUTOMATED MACHINE CONTROL AND METROLOGY This application is a continuation of U.S. patent application Ser. No. 10/227,619, filed Aug. 23, 2002 now U.S. Pat. No. 6,889,113, which claims priority from U.S. Provisional Pat. App. 60/314,687, filed Aug. 23, 2001, both of which are hereby incorporated by reference.

TECHNICAL FIELD OF THE INVENTION

The present invention relates to a graphical system for automated control of image-based operation.

BACKGROUND OF THE INVENTION

To determine the characteristics of certain objects, particularly characteristics that require instruments to observe, it is often necessary to obtain images of the object and then to perform measurements on the image. For example, microscopic structures are often viewed and measured using electron microscope images. Similarly, astronomical images from telescopes are used to facilitate measurement of large, but distant astronomical objects.

"Microfabrication" is the fabrication of extremely small structures. Microfabrication processes are used, for example, to produce structures in integrated circuits, to build magnetic heads for reading and writing to magnetic media, and to fabricate miniature mechanical or electromechanical devices. During microfabrication, it is necessary to measure critical dimensions to ensure that the process is operating properly and that the parts being produced meet the product specification.

For example, recording heads for disk drives are fabricated on ceramic wafers by a number of methods including but not limited to cutting the desired shape with a focused ion beam, photolithography and broad-beam ion etching. These devices are three dimensional and need to be managed or controlled in all three dimensions. One method of verifying that the recording heads are of the proper dimension is to cleave the wafer, that is, break it along a line running through the recording head, and measure the width of the recording head along the exposed cross-section. This method is time consuming and costly. Because many recording heads are fabricated on each wafer, cleaving the wafer results in the unnecessary destruction of many recording heads. Also, many labor intensive and time consuming steps are involved in cleaving the wafer at the correct place, placing the cleaved wafer in a vacuum chamber, and evacuating the chamber so that the recording head cross section can be viewed in an electron microscope or other viewing device.

Industry needs a simple, rapid, efficient method for performing measurements on microscopic structures and other imaged structures.

SUMMARY OF THE INVENTION

An object of the invention is to provide a simple, efficient method to graphically control machine operations.

Another object of the invention is to provide a simple, efficient method to graphically specify metrology operations.

The invention combines an image with operator controllable, computer-generated graphics, some of the graphics having operations associated therewith such that the graphics specify an operation on the image or on the object of which the image is formed.

The invention can be used for controlling systems, for example, image-forming systems such as electron microscopes, focused ion beam systems, scanning probe microscopes, optical microscopes, telescopes, and other types of microscopes; systems that can alter a work piece such as focused ion beam systems and laser beam systems; and systems that analyzes and measures images, such as pattern recognition and measuring hardware and software. The invention is particularly useful for performing multiple measurements on one or more images. For example, the invention is useful for measurements on images formed using charged particle systems, such as scanning electron, focused ion beam, transmission electron or optical microscopes. It provides a simple way to program machine operations, particularly, but not limited to, metrology operations.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and the advantages thereof, reference is now made to the following descriptions taken in conjunction with the accompanying drawings, in which.

DESCRIPTION OF THE PREFERRED EMBODIMENTS

Figure 1:
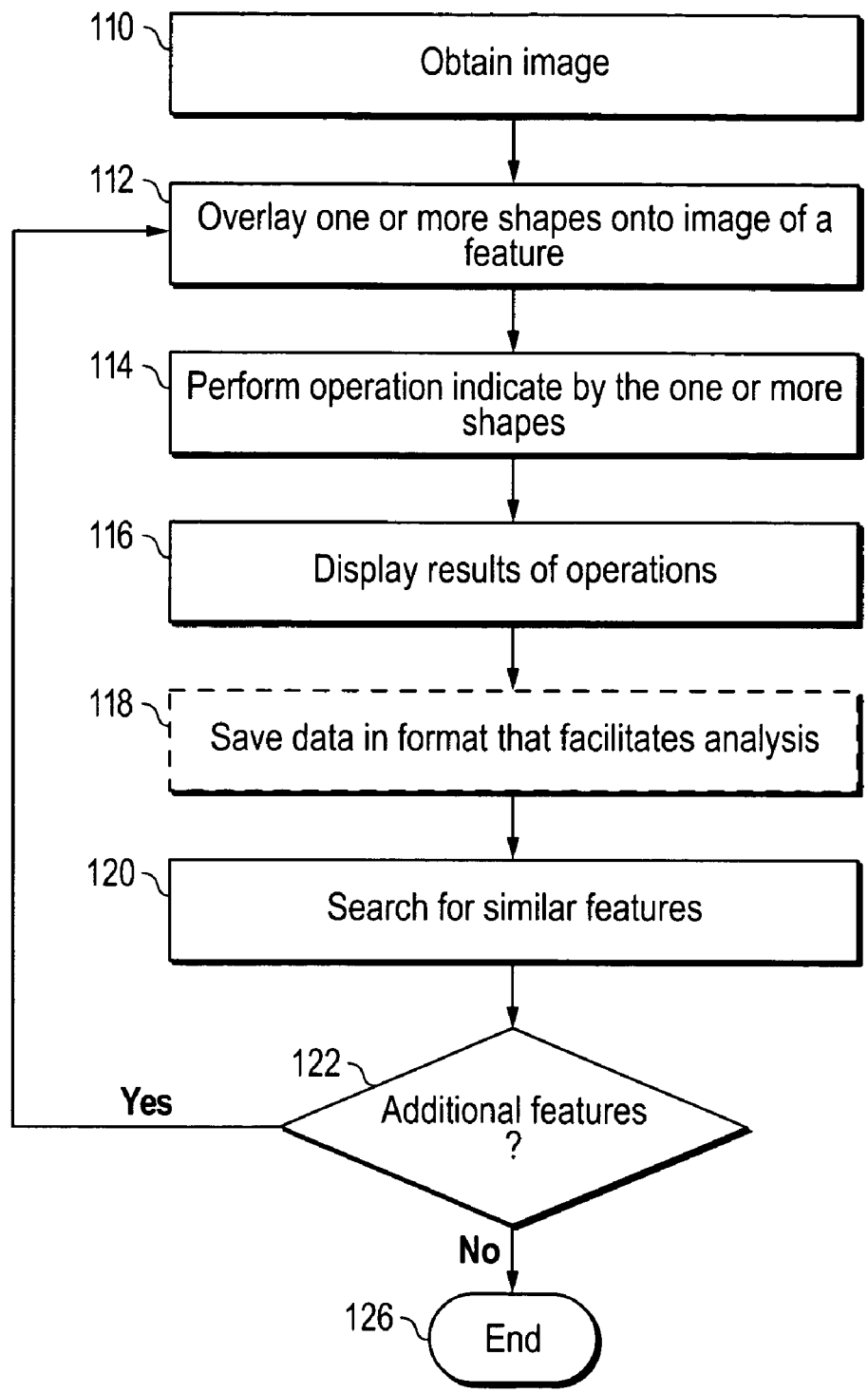
FIG. 1 is a flow chart showing steps of an embodiment of the invention.

The invention combines an image of a work piece with operator controllable, computer-generated graphics, some of the graphics having operations associated therewith such that the graphics specify an operation on the image or on the work piece of which the image is formed.

In some implementations, the invention combines imaging with computer-aided design-type software. For example, one or more images from a charged particle beam microscope are used as a background upon which are superimposed one or more graphics components, such as vector-type graphic components, generated by the computer-aided design software. The scale of the page is automatically set to the scale of the image or images that it contains. The user can then specify operations to be performed on the image or on the work piece that is imaged by manipulating the computer-aided design components.

The operations can include, for example, moving the stage of a charged particle beam system, milling a specimen, performing measurements on the displayed image of the specimen, locating patterns on the specimen, or performing additional operations at the site of the located patterns. The operations are typically performed in a specified order, and the results of measurement operations can be automatically placed in a spreadsheet, database, or other data analysis tool.

In one embodiment of the invention, a geometric shape is associated with an action. The graphic component is preferably selected from a group of predefined shapes combined into groups, called stencils, from which they can be dragged onto the image. The graphic component can then be moved, resized, rotated, or otherwise modified on the image. The position, that is, the XY coordinates, on the image at which the user places the shape determines where the action will be executed on the image or imaged specimen. The shape's area may determine an area of the operation, for example, the size of a mill-box (that is, an area on the images specimen to be scanned and milled by a focused ion beam) or an edge detection search zone (that is, an area of an image to be searched to locate an edge by detecting changes in the image brightness).

The shape contains not only the shape geometry, but also contains the tool's non-geometrical configuration, for example, edge-detection thresholds, mill-box doses and pattern matching reference images. A user can configure the shape after it is placed onto the image. A user can duplicate a shape to specify the same operation to be performed at a different location. Duplicating the shape also duplicates the non-graphical configuration allowing the user to quickly and efficiently construct a sequence of operations.

A user can combine shapes to specify a sequence of operations, thereby allowing a complex operation to be built from a series of simpler operations. Shapes can be edited as appropriate and edited shapes can be saved for reuse. A full sequence of operations can be conveniently subdivided using the concept of pages. A page groups shapes performing operations closely related to each other. Typically, this involves operations based upon or related to a given image. A sequence can have an arbitrary number of pages.

The operations associated with the graphics can be any type of operation, such as metrology operations, moving a stage, or milling the sample. Thus, a site to be measured can be prepared by, for example, cross-sectioning and imaging, and then the site can be characterized by measurement or other operations. The series of operations can then be performed on multiple sites having similar patterns as located by manually or automatically by pattern recognition software. The shapes that specify the operations can include properties, such as beam parameters, for focusing and controlling the focused ion beam systems. The operations associated with the shapes are ordered, preferably by parent-child relationships among the shapes and by other means, such as page orders, between shapes. The order can preferably be displayed, for example, on a tree or flowchart, and changed if necessary.

For example, in one embodiment, as shown in FIG. 1, an image is obtained in step 110. The image can be obtained from an imaging system, for example, from a telescope, microscope, such as a scanning electron microscope (SEM), focused ion beam system (FIB) used as a scanning ion microscope, or other imaging apparatus. The image can be "live," that is from a sample on an instrument, or the image can be "off-line," that is, stored in a file. In step 112, a user overlays onto the image one or more forms or shapes that may specify one or more operations to be performed. For example, a shape comprising a rectangle placed on the image may prescribe an operation of locating a feature edge within the rectangle. A second rectangle may be used to indicate a second feature edge location operation. A third graphics shape, such as a dimension line, placed on the image between the graphics representing the edge locating operation may indicate an operation comprising measuring the distance between the feature edges located by the previous operations.

In step 114, the operation indicated by the one or more shapes is performed. In step 116, the image or the shape is modified to indicate the results of the operation. For example, when a measurement operation is performed, the measured dimension can be displayed on the image as a computer generated graphic and optionally saved in step 118 in a format, such as a spreadsheet, that facilitates data analysis. The system can be trained to recognize patterns. In step 120, the system searches the image using pattern recognition software to locate similar features at other locations. Decision block 122 shows that if similar features are located, the process returns to step 112 to perform similar operations on the similar features at the other locations. Alternatively, the process could begin with step 114 on the similar feature and proceed automatically without displaying the image and the shapes.

In some preferred embodiments, the shapes have parent-child-type hierarchical relationships so that moving, resizing, or rotating a parent object can move, rotate, and optionally resize its children. After the system is trained at one site to match an image pattern, measurements or operations once specified can be performed automatically on similar patterns, even though the similar patterns are of different sizes or rotated. Shape parameters for child shapes at subsequent sites may be determined by formulas from automatic changes in the parent shape. A preferred user interface exposes the formulas to allow the user to fine tune the relationship. The relationship between the shapes can also specify the order of executing.

A preferred user interface allows the user to interact with both the physical (e.g., position, size, orientation) and logical (e.g., parent/child relationships) attributes of the shapes in the metrology sequence. Providing both logical and physical views allows a user to easily understand the parent/child relationship between shapes and their execution order in the programmed sequence. An arbitrarily complex sequence, containing many hundreds of tools, can be constructed purely by dragging tools onto the page. The user can preferably reorder the execution of tools of the same peer hierarchy via the sequencer tree dialog. No formal scripting, compiling or textual logical programming is typically required at any stage of the sequence construction, although in some embodiments, such programming may add flexibility.

The combination of parent and child shapes is called a "composite shape." After the user has designed a composite shape, the shape can be made into a "master" by simply duplicating the composite shape and dragging the copy on to a stencil containing pre-defined shapes. The parent/child execution relationship between the shapes is automatically asserted when the composite shape is dropped onto a drawing page. The master can be given a suitable name. The user may also edit masters on the stencil. This provides great flexibility because new masters are added without reinstalling the whole application.

The master shapes on stencils contain not only the shape geometries, but also contains the shape's non-geometrical configuration, for example, edge-detection thresholds, millbox doses and pattern matching reference images. Therefore, the custom configuration dialogs created for the shapes are also available to interact with the user when masters are created and edited. The master can be a simple or a complete set of metrology shapes including straight line fit and dimension shapes. The user only has to adjust the parameters, such as search areas, train the pattern recognition tool, and set edge recognition thresholds before the metrology is ready to be tested.

In one application, for example, an image of a ceramic wafer having fabricated thereon a thin film recording head may be displayed. A user could drag a rectangle shape onto the image that has associated operations that use contrast differences on the image to locate geometric features within the rectangle, such as the edges of the thin film head. The user could also drag dimensioning lines onto the image, the dimension lines then displaying the dimension between the identified edges to provide the width of the thin film head at different locations. The system, having been trained, can then search for and recognize the pattern of a thin film recording head, and repeat the edge identification and measurement operations at each site at which a thin head is found. The results of the multiple measurements can be automatically entered into a spreadsheet or relational database to analyze the results. Incorporating a spreadsheet or relational database can provide formula programming to perform on the fly analysis. The results can be fed back to the system to alter the sampling pattern. Thus, the invention makes possible adaptive sampling, that is, the use of previous site results to determine future sites operations. Such sampling is useful, for example, in Lithography Focus Exposure Matrix analysis in semiconductor or data storage processes.

The system can be implemented using commercially available components, such as a diagramming or two-dimensional computer-aided design (2-D CAD) program, a vision program, a data analysis program, and a charged particle beam interface program. The available components are typically customized and enhanced through add-ons and custom programmed controls. Although such an implementation is a very efficient use of programming resources, the invention is not dependent on such software and could be written from scratch by skilled programmers.

The invention makes automatic control of a charged particle beam system easy, thereby reducing engineering setup time. Configuring the system may include not only setting up sample measurements, but also setting up preparation of the measurement site, such as by milling to expose a buried feature or a cross section to be measured.

One preferred embodiment provides an integrated application that uses scanning electron microscope (SEM) image capture, metrology, focused ion beam (FIB) micromachining, and a results database. The embodiment combines a two-dimensional computer-aided design (CAD) program with a vision program to facilitate programming of beam operations and displaying the results. The CAD program produces graphics that can be overlaid onto an image to specify operations to be performed on the imaged site.

Described below is a preferred embodiment is in which a charged particle system is used to obtain an images; Visio software from Microsoft, Redmond, Wash., is used to produce shapes having associated site preparation and measurement operations; and pattern recognition software from Cognex Corporation, Natick, Mass., is used to identify features to be measured. Charged particle beam systems are controlled using the xP an application programming interface from FEI Company, Hillsboro, Oreg., the assignee of the present application.

The following terms are used in the description below:

ABS—Air Bearing Surface (part of magnetic recording head)

ActiveX control—a type of software control using ActiveX technology developed by Microsoft ADO—Microsoft ActiveX Data Objects C3D and IC3D—names for a software system embodying the invention Caliper—an pattern recognition tool from Cognex Corporation that locates edges Visio—a diagramming or two dimensional computer-aided design program by Microsoft FEI shape—a customized shape that appears on the Visio Stencil in one embodiment of the invention GEM—(Generic Equipment Model) an industry standard programming interface for interconnecting semiconductor manufacturing equipment in a fabrication plant Gizmo—an object encapsulating the combination of a shape, a tool and a control GUID—Microsoft Globally Unique Identifier HFW—Horizontal Field Width MDI—multiple document interface MUIF—FEI's manual user interface. A panel comprising of knobs that allow the user to manual set microscope parameters OCX files—Files containing controls associated with the OLE (Object Linking and Emdedding) standard PatMax—a pattern recognition tool available from Cognex Corporation as part of a VisionPro library or other product Sequencer—a controller that controls the sequence of operations the system is to perform.

STACOM map—FEI's Stage Position Compensation/Correction application.

Stencil—Place holder for pre-configured shapes or groups of shapes.

UI 1280—an computer interface from FEI for controlling the operation of charged particle beam systems VBA—Visual Basic for Applications—a Microsoft object-oriented programming language for supplementing applications XML—Extensible Mark-up Language xP—an application programming interface (API) from FEI for controlling the operation of charged particle beam systems.

The embodiment described below, referred to as C3D or IC3D, is implemented using commercially available software components that allows user extensions. The shapes associated with the operations are custom shapes created using Visio. Vision operations, such as pattern recognition, is performed by VisionPro software from Cognex Corporation. A Formula One spreadsheet from the Formula One Division (formerly Tidestone Technologies) Overland Park, Kans., of Actuate Corporation, Kent, England, can be used for data analysis. The interface used for controlling the charged particle beam system is preferably the xP programming interface from FEI Company, Hillsboro, Oreg., the assignee of the present invention and manufacturer of focused ion beam systems and electron microscopes. Custom controls for the various components and interfaces between the components can be programmed using VBA and ActiveX.

In this embodiment, one or more Visio pages contains the metrology configuration. A page is the canvas on which the metrology configuration is designed. The user will begin by inserting a bitmap (or TIFF) image of the feature to be dimensioned. Since Visio is a simplified CAD program, it provides a drawing scale. The header or tags in the image file contains the image scale in pixels per meter, thereby allowing the Visio page drawing scale to be appropriately set when an image is loaded.

It is convenient to insert the image into Visio so that the programmer can use it as guide when overlaying shapes onto it. Once programmed, operations can be performed automatically on subsequent sites without displaying an image. The image pixel data is used as an input to the Cognex tools that can be associated with the Visio shapes to perform operations without displaying the image.

In one embodiment, the image is combined with the page, only allowing one image to be associated with each page. In other embodiments, such as one in which a sample is analyzed by cutting and imaging multiple cross sections to obtain a three-dimensional characterization, more than one image per page may be required. It is therefore preferable in some implementations to make the image tool a shape that would be dragged off the stencil and placed upon the page. Imaging is described in more detail below.

Visio shapes can be associated with run time behavior as described in more detail below. Visio provides a published object model that facilitates connecting FEI designed ActiveX Components to a Visio instance. Once connected, Visio documents, pages, and shapes can easily be manipulated, by custom-designed components, using the properties, methods, and events made available by Visio. Thus, Visio objects can control operations outside of Visio and operations outside of Visio can control Visio objects.

Each Visio shape is described in its own ShapeSheet spreadsheet, which contains information about the shape's geometry and its other properties. For example, the ShapeSheet spreadsheet contains a shape's dimensions and the x- and y-coordinates of each of its vertices. Much of the information in the ShapeSheet can be defined by using formulas rather than hard-coded numbers. By using formulas, a shape can behave differently depending upon its context. A formula can include standard mathematical and logical operators and functions. A few user-defined cells are added to the ShapeSheet for some shapes to identify the shape when it is dropped on to a page.

A central part of Visio is the stencil, which typically contains shapes having related functions, such as dimensioning or flow charting. The user can build complex diagrams by dragging shapes off the stencil and dropping them on to the page of a Visio document. The shapes on the stencil are called masters. The Technical and Professional versions of Visio provide a number of useful shapes, such as the dimension shapes on the standard Annotations\Dimensioning Engineering stencils.

It is typically required to create a number of custom shapes to implement the invention using Visio. For an embodiment used for metrology, the custom shapes used can typically be divided into several major groups, including microscope shapes, vision shapes, dimension shapes, fit shapes, intersection shapes, and VBA shapes Microscope shapes provide the behavior for a physical system, such as a charged particle system, optical microscope, or a dual (electron and ion) beam system. The behavior associated with these shapes includes, among other things, imaging, milling and moving the stage. The image shape is complex and typically requires the whole page area. The image sets the page scale based upon the magnification. The mill shape can be a simple rectangle that is sized by the image magnification. Preferably, the mill shape can be resized by the user and can be of various geometric shapes. The move shape is a 1-D shape connecting a feature's source location to a destination location, typically the center of the field of view. Using microscope shapes, the invention can provide not just a graphical metrology tool for use on a final image, but a total site processing solution.

Vision shapes locate a feature or edge. When a shape is created by dragging a master onto the page, the user is prompted to provide a name for the shape to make the shape easier to identify later. An appropriate component object is instantiated and associated with the shape. The associated configuration dialog is also docked inside the page. The user can configure the shapes search area, model area, origin connection point etc. In one preferred embodiment, the component objects are vision tools provided by VisionPro software from Cognex Corporation. Since the Cognex display is preferably not used, all of the drawing requirements associated with the Cognex tool are replicated in the Visio shape. Vision shapes include, for example, PatMax (Cognex VisionPro PatMax), Caliper (Cognex VisionPro Caliper), Radial Caliper (Cognex VisionPro Caliper), Skew Caliper (Cognex VisionPro Caliper), and Blob (Cognex CVL GBlob).

Dimension shapes provide an actual measurement of a feature on the image, either distance, angularity or a point. The point shape returns two values, X location and Y location of the point. When a dimension shape is created by dragging it onto the page, the user is prompted to provide a name for the shape as this makes shape easier to identify later. A column for each dimension is preferably automatically added to the results spreadsheet containing the shape's name, and in the case of multi-dimensional shapes, the dimension name.

Examples of dimension shapes can be found on the Visio Annotation\Dimensioning—Engineering stencil and include: horizontal, horizontal outside; vertical; vertical outside; aligned out even; aligned out uneven; aligned even; aligned uneven; arc radius; radius outside; radius; diameter; diameter outside; angle center; angle uneven; angle even; angle outside; and point (location of a point referenced to the image coordinate space)

Fit shapes are used to connect Vision shapes to dimension shapes. Examples are line fit, circle fit and line extension.

When a fit shape is created by dragging it onto the page, the user is prompted to provide a name for the shape as this makes shape easier to identify later. The user must identify connection points from either vision shapes or other connection shapes to connect too. Examples of fit shapes include line extension, least squares line fit, and circle fit.

Intersection shapes maintain a connection point at the intersection of two connection shapes, such as connection lines. The intersection point of two connection shapes is very useful location and can be readily calculated based upon attributes in the ShapeSheets of the shapes. Intersection shapes will be preferably automatically generated for all Connect shape intersections of the drawing. Intersection shapes will be located on the page. Refresh methods may be used to calculate and place the Intersect shapes or the Visio Idle Event may be capable of being used as a trigger.

As an illustration of one such custom shape, a Visio PatMax shape can control a PatMax® vision tool from Cognex Corporation. The PatMax shape can be derived as a copy of the rectangle shape on Visio's Basic Shapes Stencil. Properties of a Visio shape are defined in a user-accessible spreadsheet called a ShapeSheet. When a PatMax shape is derived from a basic rectangle, custom-defined cells are added to the shape's ShapeSheet to identify it when it is dropped on to a page. A Shape Manager control is preferably created to manage the association of shapes and behavior objects, such as the PatMax vision tool.

The user can configure the PatMax shape, which in turn configures the Cognex PatMax tool. For example, the shape's rectangular area sets the PatMax model area and a connection point can be used to indicate the origin of the model. A connection point is a Visio feature that allows a user to glue endpoints of 1-D shapes to a 2-D shape. Visio provides the user a Connection Point tool to place connection points on a shape. The user can therefore manipulate the shape to set the search area and origin. The PatMax tool requires more configuration than just a model area and origin, so a configuration dialog is preferably displayed when the PatMax shape is dropped onto the drawing, so that the user can set various thresholds and operating modes.

The PatMax shape is used to train the PatMax tool before it is executed. After the PatMax tool has been executed, the PatMax shape is redrawn based upon the execution results of the tool. That is, not only does the user use the Visio shape to program the tool, the results of the operation of the tool can then alter the Visio shape. For example, the PatMax X Location and Y Location results are typically used to relocate the shape on the page. The model origin is represented by the shape's sole connection point. PatMax can match patterns even if the size or orientation is different from that of the original is changed. If a located pattern is of a different scale than the original shape, the X Scaling and Y Scaling results from the PatMax tool will be used to resize the shape. The angle result will reorient the shape. The Score, that is, how well the located pattern matches the original training pattern, can be used to change the color of the shape outline. The concept of redrawing the shape based upon the run time results is implemented through the relationship of parent and child shapes. Skilled persons will be able to implement other shapes based on the PatMax example described above.

The concept of redrawing the shape based upon the run time results is facilitated by the relationship of parent and child shapes. Thus, the invention provides an adaptive tool in which the behavior of the shape varies with the result of a previous operation, such as the PatMax operation of locating a pattern and returning location, scaling, and rotation information about the located pattern.

Shapes can be connected together to form datum points, that is, points to be used for measuring dimensions. Thus, a metrology process can comprise first operating on an image to locate datum points and then measuring distances between fixture points. The Visio document can be used for configuring the whole site activity, including site alignment and cross sectioning.

For example, thin film head metrology may use a PatMax tool to locate the pole of the head and then use caliper tools positioned a set distance from the pole to locate edges that together define the width of the head. Defining such relationships is sometimes called "fixturing." Shape fixturing can be achieved by using Visio's shape grouping. A group is made up of at least one parent shape and one child shape. Child shapes follow their parents. When the PatMax tool associated with the parent is executed, the results of the execution can be fed back to redefine not only the parent, but also the child shape's geometry for the current site being processed.

As an example of an application of the concept, one dimensional (1D) shapes can be stretched between Visio connection points positioned by PatMax or Caliper Tools. These stretched 1D lines can then be used as parents for child shapes that can be positioned at a percentage length along the 1D line and a percentage distance from the line. This provides the scale by which the user can measure, for example, a feature's width at a percentage of the feature's height. Using this technique the 1D line will automatically stretch to cover features of varying height or width without the user having to reprogram the metrology configuration.

Figure 2A:
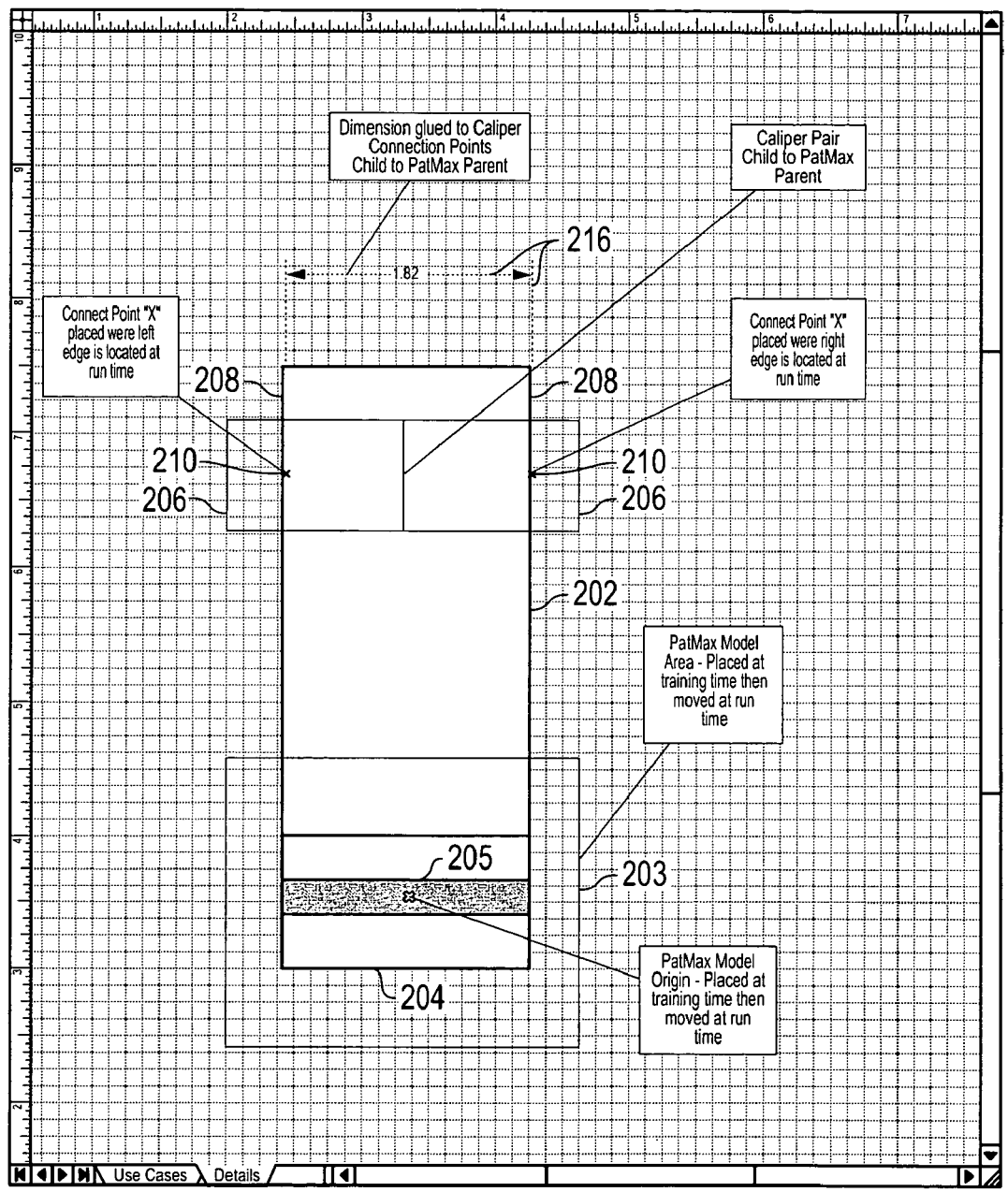
FIGS. 2A-2D show examples of metrology shapes used to measure a thin film recording head.

FIG. 2A shows an example of a combination of shapes used to measure the width of thin film recording heads. An image of a thin film head 202 is displayed. A PatMax shape 203, associated with a Cognex PatMax object, is placed over a portion of thin film head pole 204. The PatMax shape is characterized by an area and an origin 205. The area and origin are originally positioned and adjusted by the user when training the PatMax object, and then the origin is automatically repositioned and the area is automatically repositioned, resized, and reoriented as necessary when the shape is executed. Two caliper shapes 206 are positioned a predetermined distance above the PatMax shapes 204. Each caliper shape 206 is associated with a Cognex Caliper object, which searches within its area and in its configured direction to find a change in contrast indicating an edge 208 within the feature. Each caliper shape includes a connection point 210 that is automatically positioned on the located edge. Connection points are used to connect shapes together. They are most useful when used to connect together 1-D and 2-D shapes.

Dimension shapes can be connected to the connection points of calipers. FIG. 2A shows that a dimension line 216 is added to the drawings to connect to two connections points 210. The dimension between connection points 210 is automatically calculated.

Figure 2B:
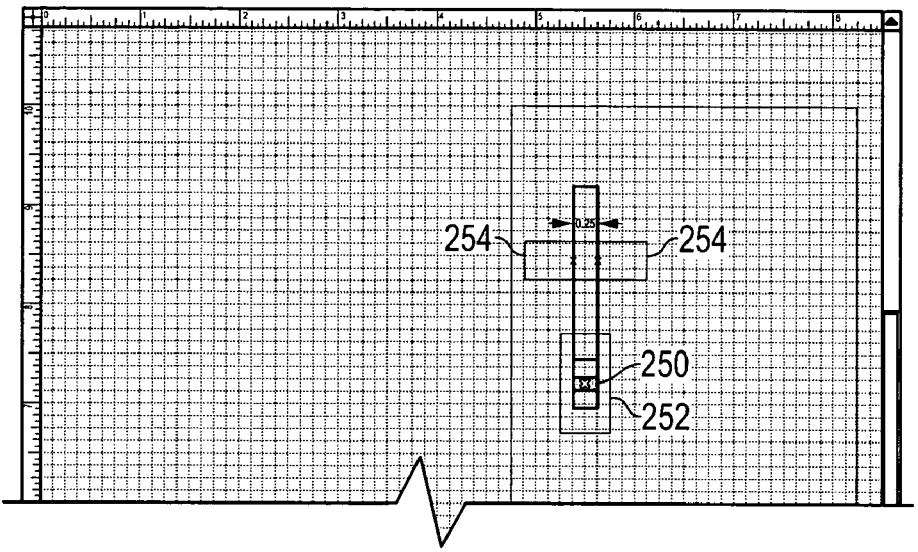

Caliper shapes 206 and dimension line 216 are defined as child shapes of PatMax shape 204 so that when the shape is applied to an image, the child shapes will locate with the parent shape. The child shapes can optionally be set to re-size or re-orient with the parent shape. FIG. 2B shows an example in which a PatMax tool object locates a thin film head pole 250 and repositions and rescales the PatMax shape 252 over the pole 250. In FIG. 2B, PatMax shape 252 is thinner than PatMax shape 204 in FIG. 2A because the thin film head pole 250 is thinner than pole 204 in FIG. 2A. PatMax shape 254 is also moved to the left, because the thin film head pole 250 is not in the center of the field of view.

Figure 2C:
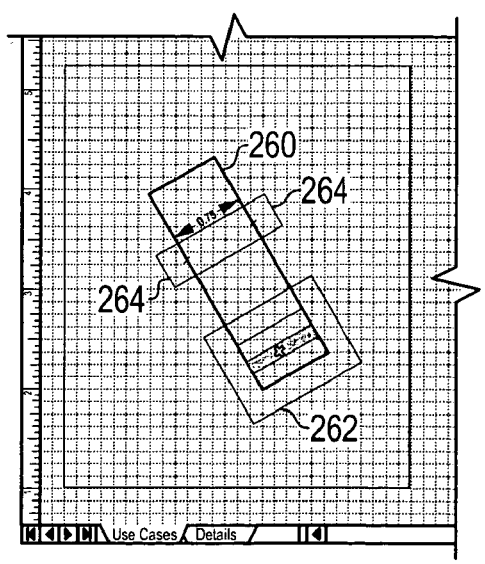
Figure 2D:
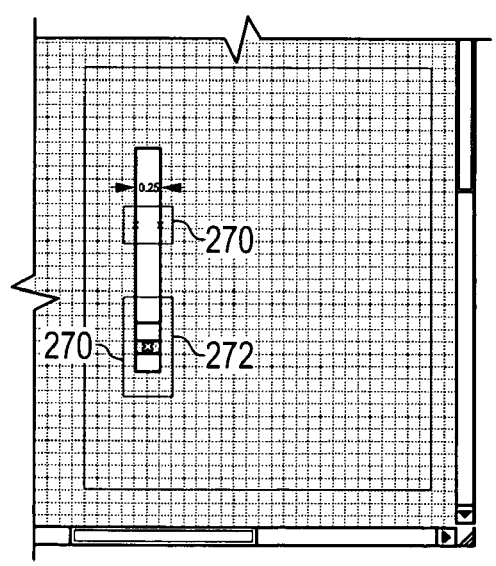

Calipers 254, which are child shapes to the parent PatMax shape 252, have relocated with PatMax shape 252, but, in this example, calipers shapes 254 were not configured to automatically re-size. In FIG. 2C, the PatMax object tool located a thin film head 260 that was rotated. PatMax shape 262 automatically reorients itself and its child caliper shapes 264. FIG. 2D is similar to FIG. 2B, but the caliper shapes 270 are configured to resize with the PatMax shape 272.

The order in which shapes are executed is as important as their XY position on the page. The execution order can be determined by the order that the shapes are placed on the page, but restricting execution to that order is limiting. Because parent shapes control the position of the children shapes, parent shapes typically execute first.

Visio's open architecture allows AddOns to access Visio's internal data collections. A sequencer can therefore be programmed to iterate through the shapes located in a page's shape collection to determine an order of execution. The sequencer that controls the operations on the charged particle beam or other imaging system is preferably capable of sequencing based on the Visio shapes.

Since it is difficult to ascertain the parent child relationships by just looking at the shapes on the Visio page, a tree control can be used to display the shape relationships. The tree control also allows the user to change the run time order of shapes that occupy the same level in the hierarchy. In most applications, parent-child relationships can be altered on the page and not using the tree control.

The functionality of milling alignment, milling, measure alignment, measure and any other operation can be each be executed by a Visio page. Visio does not specify a limit on the number of pages that a document can contain. The user can also add shapes that perform no actions, such as shapes that contain text that indicate, for example, the product type or some kind of operator instructions. These shapes are not part of the metrology sequence, but the Sequence Tree will still show their parent-child relationship to the page.

Custom shapes can be divided into two categories, active and passive. Active shapes are associated with some executable run time behavior. Examples are shapes in the group of microscope shapes. Passive shapes have no executable behavior, they only react to part of their geometry being moved by the result of an active shape. Examples of passive shapes are dimensions shapes, fit shapes and intersection shapes.

Visio is supplied with Visual Basic for Applications (VBA). VBA allows an applications engineer to construct their own custom operations by associating custom behavior with a master shape on the stencil. These shapes can then be placed upon the page and their execution position set in the sequence tree. Passive shapes have no executable behavior; they only react to part of their geometry being moved by the result of an active shape.

The sequencer will execute only active shapes and VBA shapes, which are described below. All others will be ignored. The sequencer tree preferably has two modes of display; one showing all of the documents shapes, the other only displaying active shapes and VBA shapes.

ActiveX Components connected to a Visio instance can be used to accomplish the desired run time behavior. Once connected, these Visio documents, pages, and shapes can easily be manipulated by the ActiveX components, using the properties, methods and events made available by Visio. Visio is what Microsoft terms a Multiple Document Interface (MDI) application, that is, a single instance of the application can have multiple documents open simultaneously. The Visio object model provides methods to add windows to either the MDI frame or the document windows. The functionality can be incorporated into a multi-form ActiveX control. Each of forms is docked inside a Visio window. Visio also provides methods to add custom menus and toolbars.

An FEI Tool collection of metrology-related or charged particle beam-related shapes with associated operations enables the application to perform automated metrology or other operations by executing the FEI Tools in the correct order. The execution order of the FEI Tools is set by the hierarchy defined by the user grouping shapes together. The order of execution is determined in general by the sequence of Visio pages and the parent-child hierarchy within a Visio page.

FIG. 3A shows a typical Visio screen in accordance with the invention. The page includes a scanning electron microscope image 302 in a primary window 304 and shapes superimposed over the image. The user begins by identifying a source. The image source may be an imaging instrument or a pre-defined bitmap image. The image header typically contains scaling in pixels per meter allowing the page drawing scale to be set when an image is loaded. Surrounding the image can be several optional windows (or forms) containing additional information, including a shape stencil 306, an image window 308 for selecting images to display in the primary window, a recipe window 310 that includes recipes, that is, complete metrology sequences that can be applied to a site, and a sequence window 312 that shows the sequence of execution of the shapes in the primary window. Screen 300 also includes Visio toolbars 320, which include standard and customized selections, and a Visio menu bar 322.

Figure 3:
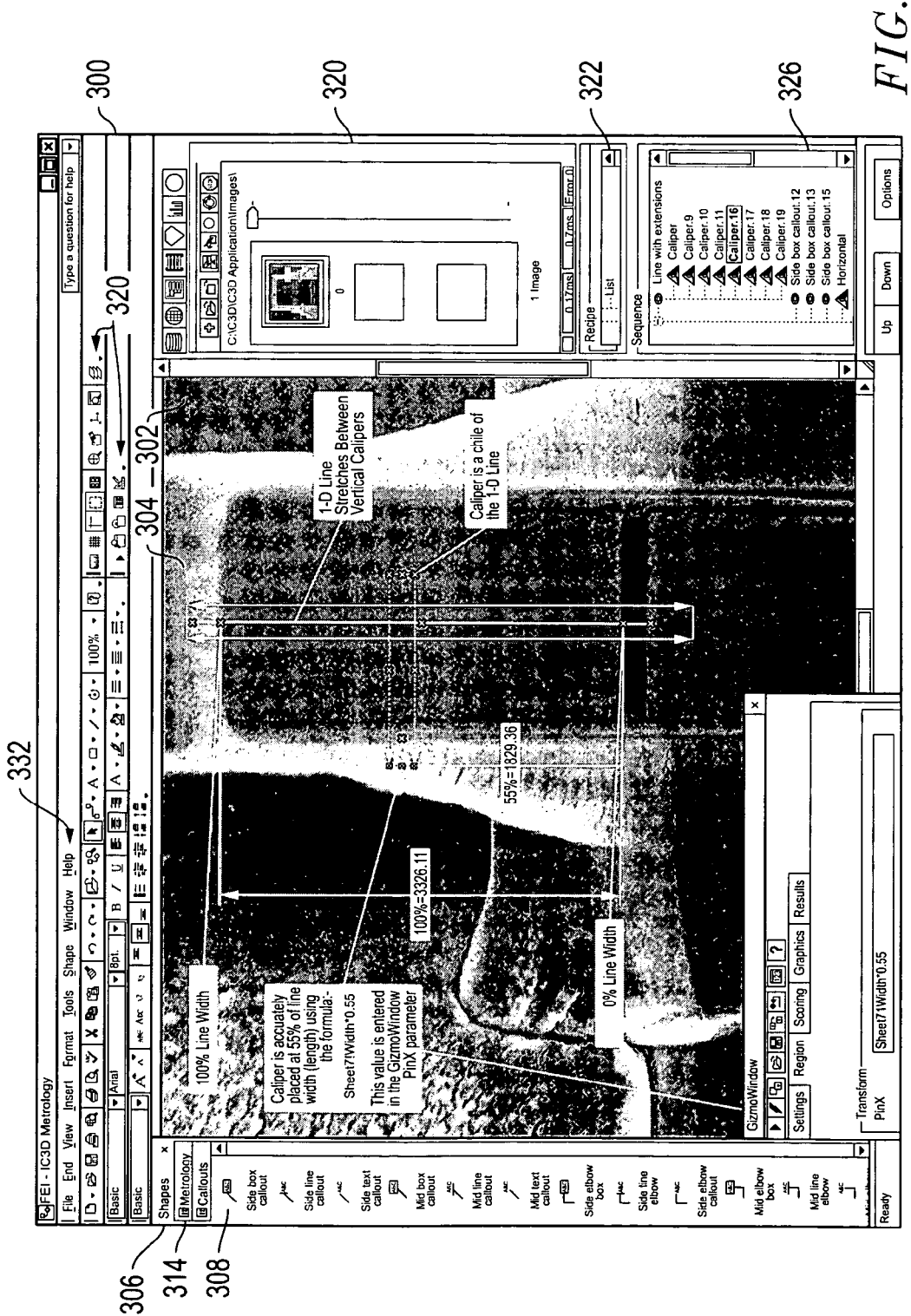
FIG. 3 shows an example of a screen display of a computer running software in accordance with an embodiment of the invention.

FIG. 3 shows a Visio screen 300 having multiple windows and toolbars. Primary window 302 displays an image 304, in this example, a portion of a thin film recording head such as those used in disk drive heads. Window 306 is a stencil window showing a stencil 308 of call-out shapes. As described above, master shapes on a stencil can be dragged onto the primary window 302 using a mouse. Combinations of shapes on primary window 302 can be dragged back onto a stencil to create a new master shape. Below call-out stencil 308 is a metrology stencil 314 having additional shapes, including for example, a PatMax shape and a Caliper shape. Different stencils and shapes can be created for different applications.

Screen 300 also includes an image preview window 320 that displays images that the user can chose to display in primary window 302. Below image preview window 320 is a recipe window 322, which contains different recipes, each recipe comprises a sequence of steps displayed in a sequence window 326. Sequence window 326 displays the order in which operations associated with shapes in primary window 302 will be executed.

Figure 4:
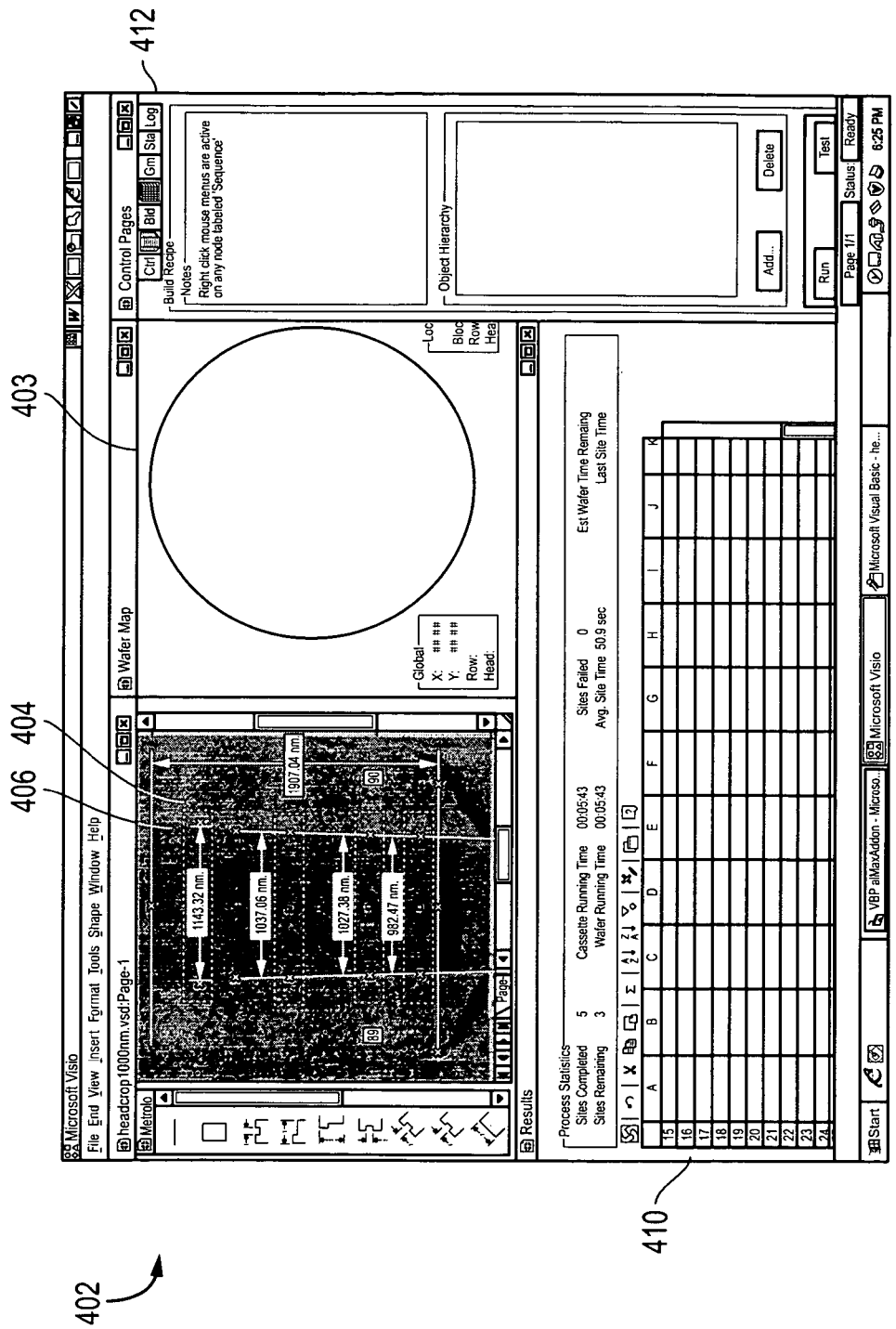
FIG. 4 shows another example of a screen display of a computer running software in accordance with an embodiment of the invention.

FIG. 4 shows a Visio screen 402 having different windows displayed, including a wafer map window 403 that shows the area of the wafer from which an image 404 in primary window 406 is located. Screen 402 includes a results window 410 for showing the measurement results and process statistics, and a control window 412 for displaying a build recipe and an object hierarchy.

Figure 5:
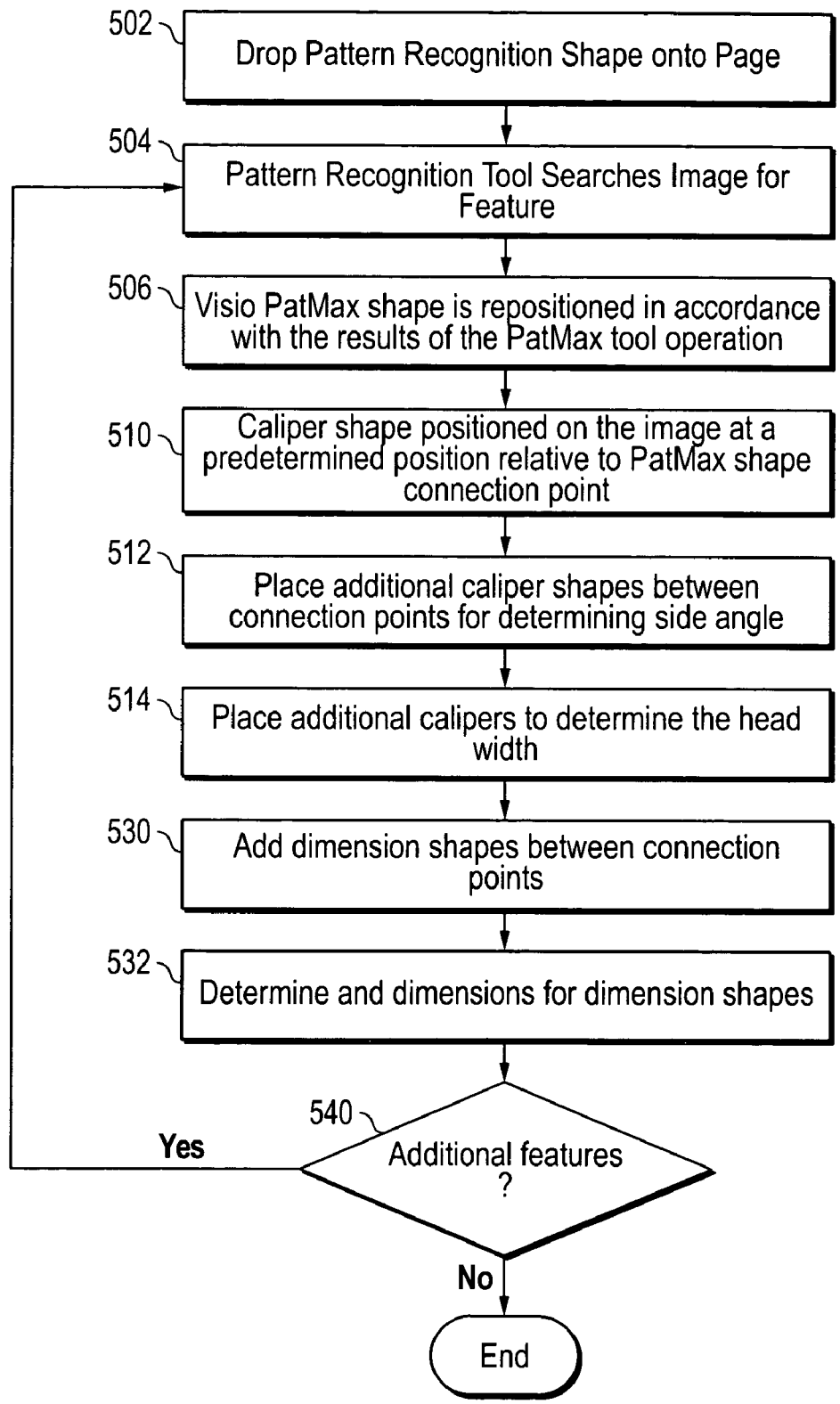
FIG. 5 is a flow chart showing steps of another embodiment of the invention.

FIG. 5 is a flow chart showing the steps used to build the metrology applications shown in FIG. 6A-6H. Skilled person will recognize that the some of the steps described in the flow chart occur simultaneously and the steps are not limited to the order shown. In step 502, a user drags a Visio shape corresponding to a pattern recognition tool, such as a PatMax tool, onto an image. The pattern recognition tool was previously trained to recognition the outline of the feature, such as a thin film recording head, to be located and measured. The pattern shape is activated, either by dropping or by double clicking, and in step 504, the tool searches the entire image or a specified portion thereof to locate the feature of interest.

Figure 6A:
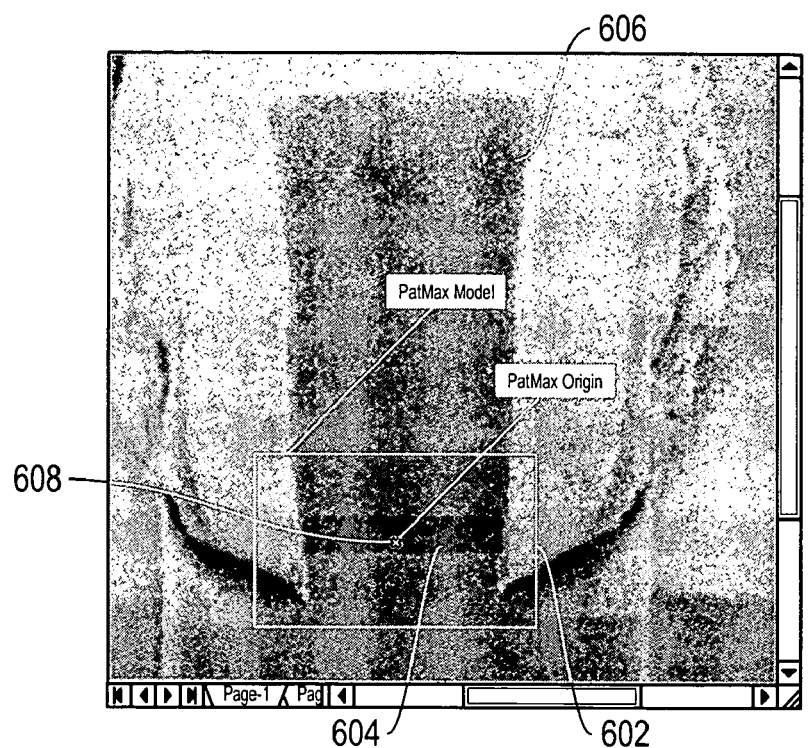
FIGS. 6A-6F show the progression of a metrology model created in accordance with steps in FIG. 5.

In step 506, the Visio PatMax shape is repositioned in accordance with the results of the PatMax tool operation. FIG. 6A shows that the PatMax shape 602 is positioned over the pole 604 of a thin film recording head 606, with a Visio connection point 608 positioned at the origin returned by the PatMax tool. In step 510, a Caliper shape 610 (FIG. 6B), which is a child shape to the PatMax shape 602, is positioned on the image at a predetermined position relative to PatMax shape 602 connection point 608. The caliper 610 search area can be scaled and oriented in accordance with the scale and angle results returned by the PatMax shape. Caliper shape 610 locates the top edge of the thin film head 606 and the top edge of pole 604 and positions connection point, 612 and 614, respectively, at the edges. Caliper shape 610 may only locate a single edge, so two caliper tools may be required, one to locate each edge.

Figure 6B:
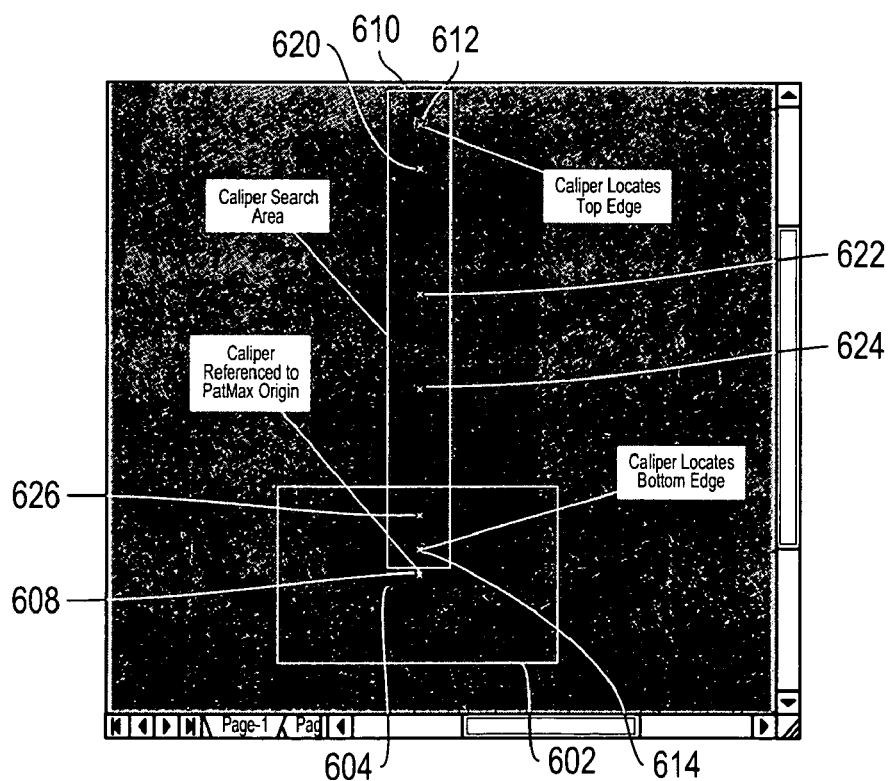
Figure 6C:
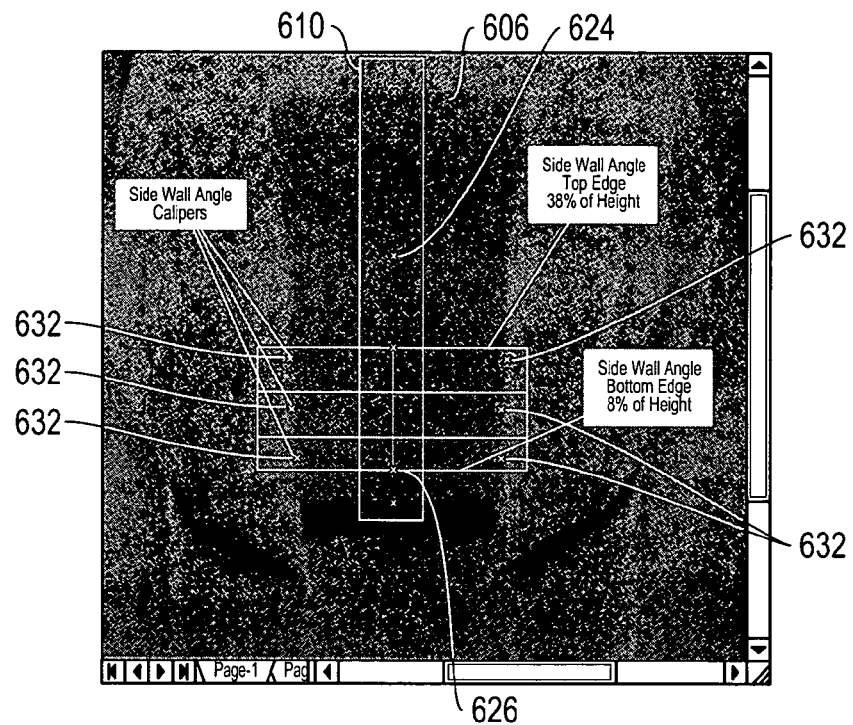
Figure 6D:
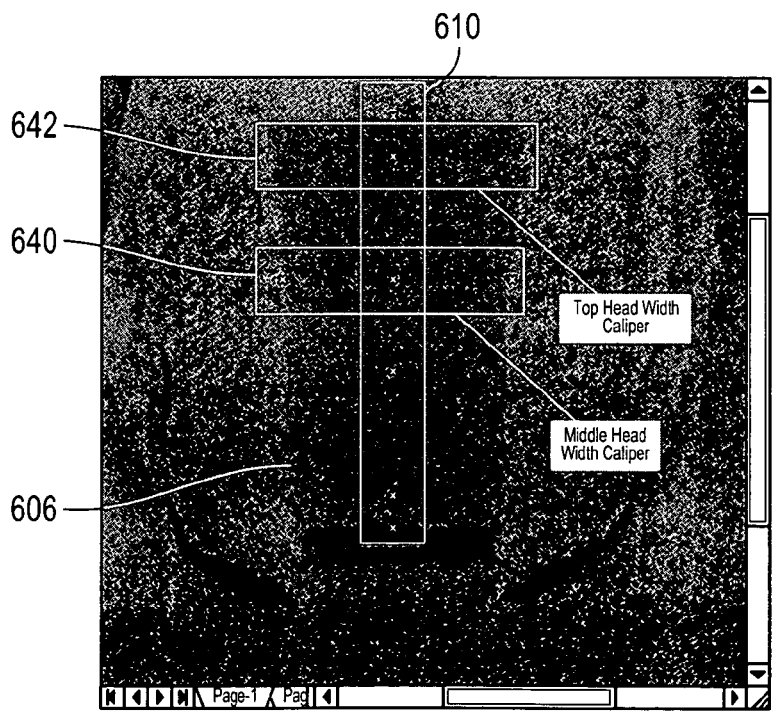
Figure 6E:
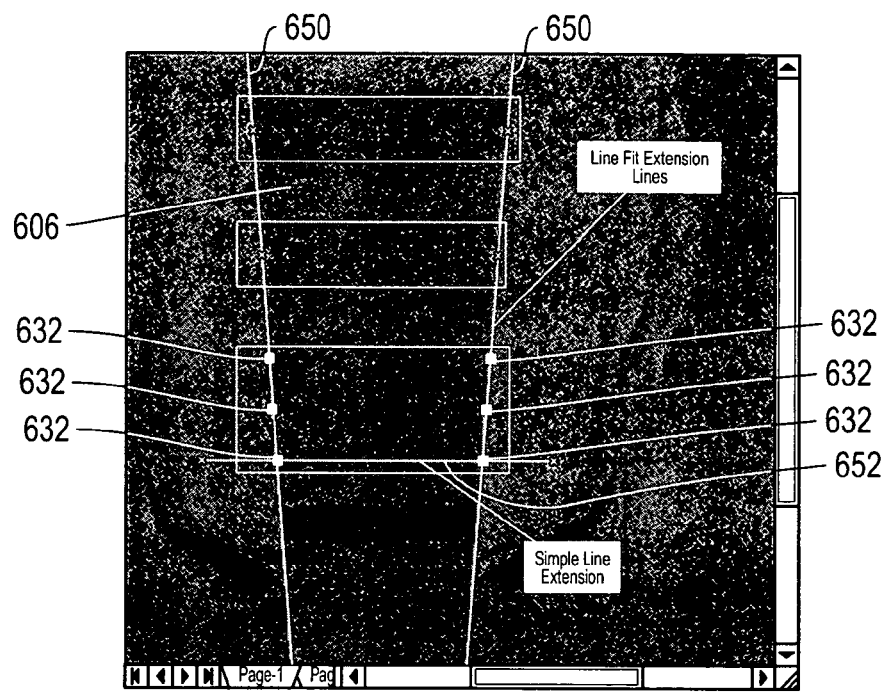

Referring also to FIG. 6B and FIG. 6C, caliper shape 610 also includes connection points 620, 622, 624, and 626. Each of these connection points is positioned at a predetermined fraction of the distance between connections points 612 and 616, this distance representing the height of thin film recording head 606. In step 512, three additional caliper shapes 632 are positioned between connection points 624 and 626. Although only three calipers are shown, five calipers (or ten, if the caliper locates only the edge on one side) would be used between eight percent and thirty eight percent of the thin film head height. These calipers locate and place connection points 632 on the edges of head 606. These connection points will be used to determine the angle of thin film head 606.

In step 514, two additional calipers 640 and 642 (FIG. 6D) are added to determine the head width. Calipers 640 and 642 are located at 50% and 95% of the height of the head 606. In step 530, a line 650 (FIG. 6E) is fit to the set of three points 632 on each side of head 606. Another, horizontal, line 652 is fit to the bottom points 632 in step 530.

Figure 6F:
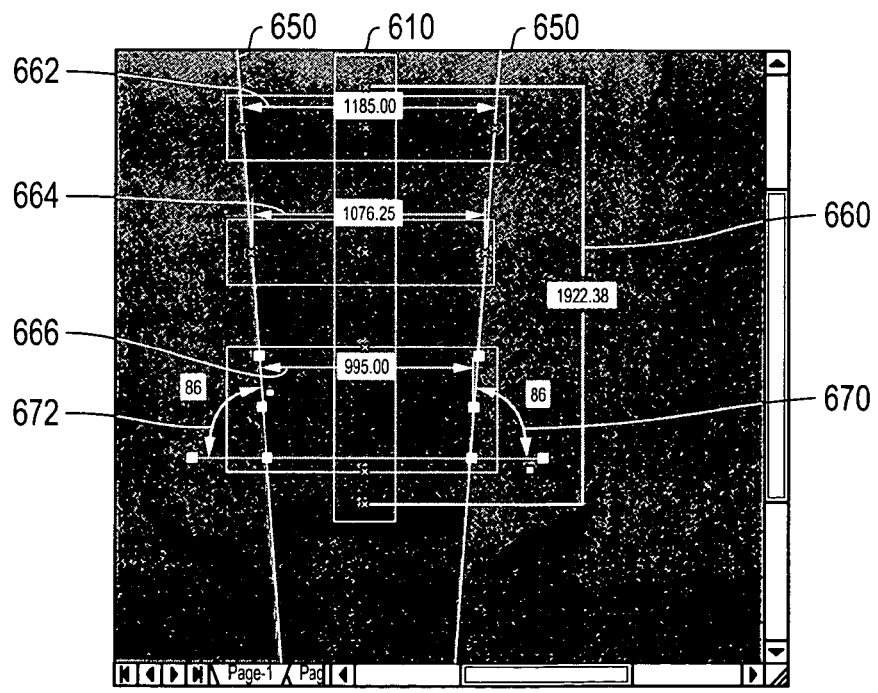

FIGS. 6A-6E show the process of locating features and establishing connection points or lines between the features. In FIG. 6F, dimensions lines are added to the drawing in step 530 and in step 532 actual dimensions are determined and displayed. Dimension line 660 automatically determined the height of the head 606 and displays the height. Dimension lines 662, 664, and 664 determine and display the width of the head at various heights relative to the total height of head 606. Angle dimension shapes 670 and 672 determine and display the head side wall angle as determined by the angle between lines 650 and line 652.

Steps 500 to 514 entail locating features and establishing fixture points; step 530 and 532 entail measuring between fixture points. Dimension can be determined for some features before fixturing of all features are completed. The congruence in scale between the image and the Visio page facilitate using Visio shapes to measure real features. The system determined in decision block 540 whether there are additional heads to measure. If there are, the sequence is repeated. It is not necessary for an image of each head to be displayed; the measurements can be performed without operator intervention.

Figure 7A:
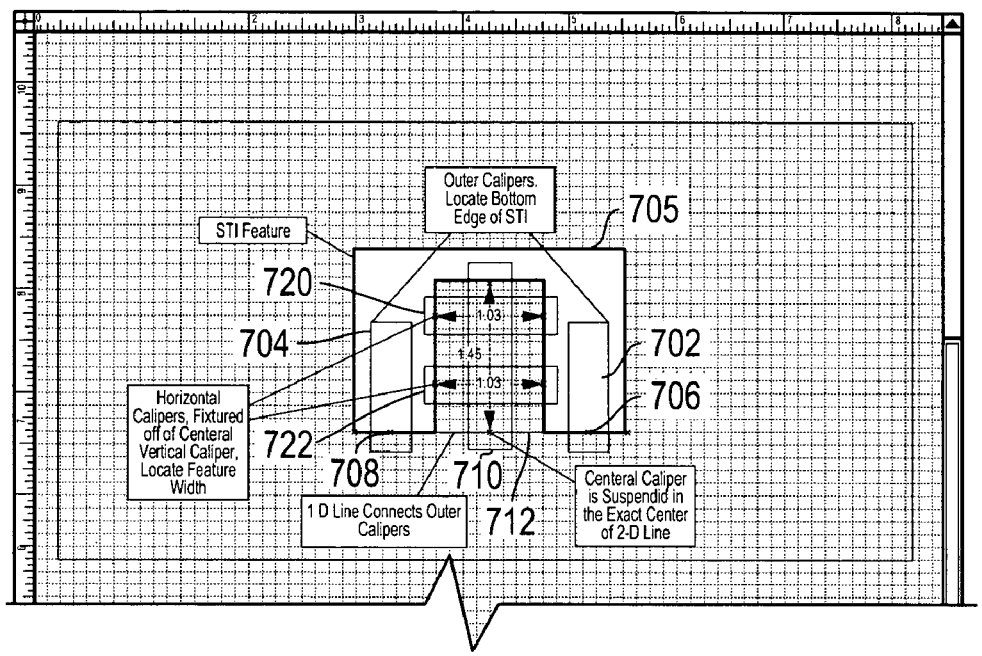
FIGS. 7A and 7B show a model for measuring suspended shapes in accordance with another embodiment of the invention.
Figure 7B:
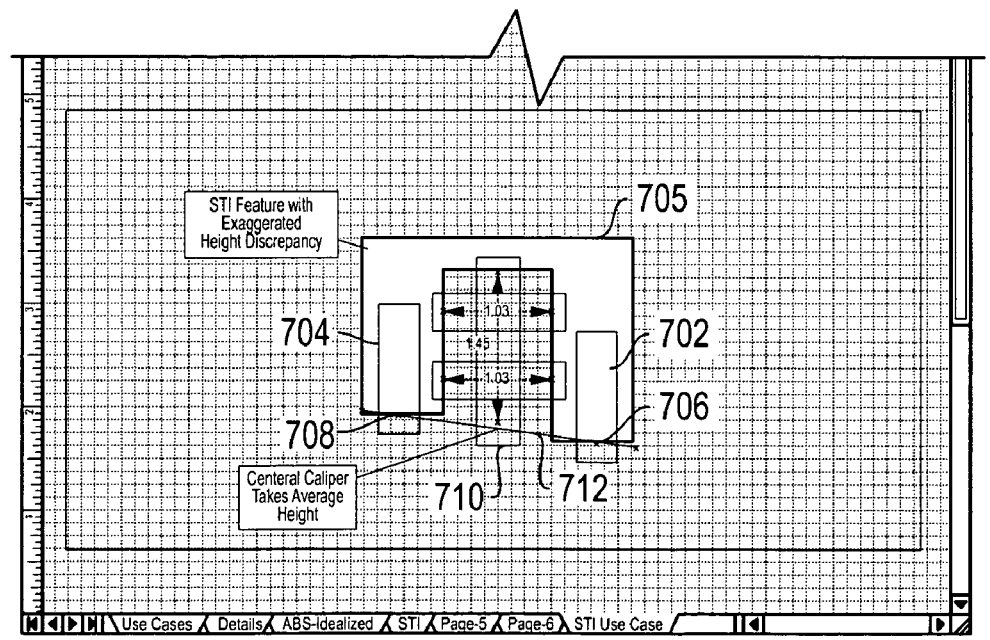

FIGS. 7A and 7B are examples of another metrology configuration for measuring a "suspended" shape, a shallow trench isolation feature in the example, that has no feature from which to fixture one end of a caliper. Calipers 702 and 704 locate bottom edges of a feature and position connection points 706 and 708 on the edge. A central caliper 710 is suspended between the midpoint of a 1-D line shape 712 between points 706 and 708. Horizontal calipers 720 and 722 are then fixtured off of a central caliper 710 at specified percentages of the caliper height. FIG. 7B shows that the metrology configuration can still function even when there is a height difference Some embodiments of the invention achieve more flexibility by isolating the finding features from measuring features. For example, Caliper and PatMax tools provide Visio connection points at features of interest to the user. The user can then snap dimension shapes onto these connection points. Thus, it is possible to measure the distance or angle between discontinuous features. For example, an image of a first portion of a field of view can be obtained and a first feature located in the first portion. An image of a second portion of the field of view can be obtained and a second feature located in the second portion. The PatMax tool that locates each of the features attaches Visio connection points onto the image of each of the features.

A one dimensional Visio dimension line shape can be connected between the connection points and the measurement between the two features is determined, displayed, and optionally saved in a database or spreadsheet. It is not necessary to form a continuous image between the two features. In some applications, such as transmission electron microscope (TEM) sample preparation, imaging can degrade or destroy the specimen. The invention facilitates measuring across the sensitive area without imaging and thereby damaging the intermediate area. FIGS. 8A-8F show a sequence of operations that can be used in accordance with the invention to prepare a sample for a TEM without damaging the sample. Other such applications facilitated by the invention will occur to skilled persons and do not depart from the scope of the invention.

Figure 8A:
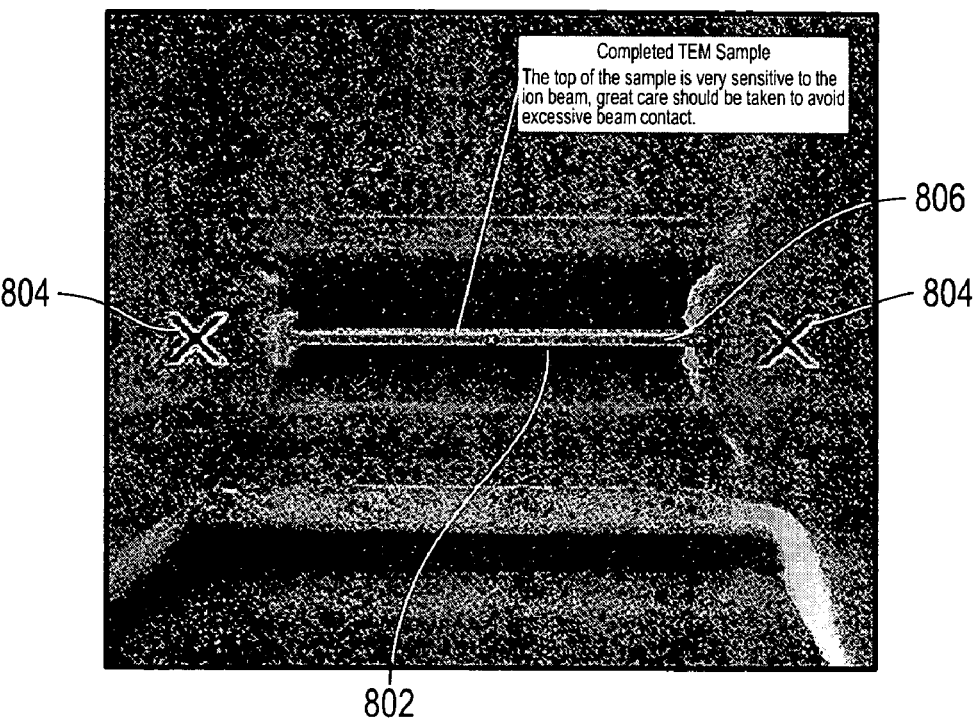
FIGS. 8A-8F show the progression of a metrology model for measuring and milling a transmission electron microscope sample using a non-continuous image.
Figure 8B:
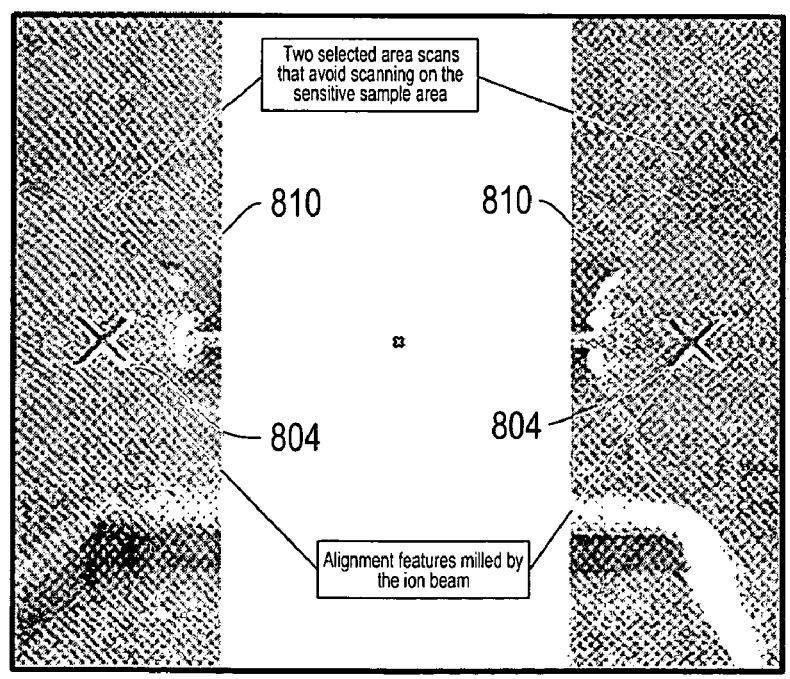

FIG. 8A shows a typical TEM sample 802. An "X" has been milled on both sides of the sample as a reference mark 804. It is desirable to thin the TEM sample using a focused ion beam, but the top portion 806 of the sample is fragile and readily damaged by exposure to an ion beam. Even brief exposure to the beam during imaging operation can damage the sample, so ion beam imaging is minimized. The invention allows the TEM sample to be thinned using an ion beam by accurately scanning the ion beam while minimizing exposure of the top of the sample to the beam. FIG. 8B shows an image produced by an ion beam than avoid scanning the center portion of the TEM sample. The beam scans a rectangle 810 on either side of the sample, but either the beam is blanked at the central area, or the beam jumps from the last dwell point on one side to the first dwell point on the opposite side.

Figure 8C:
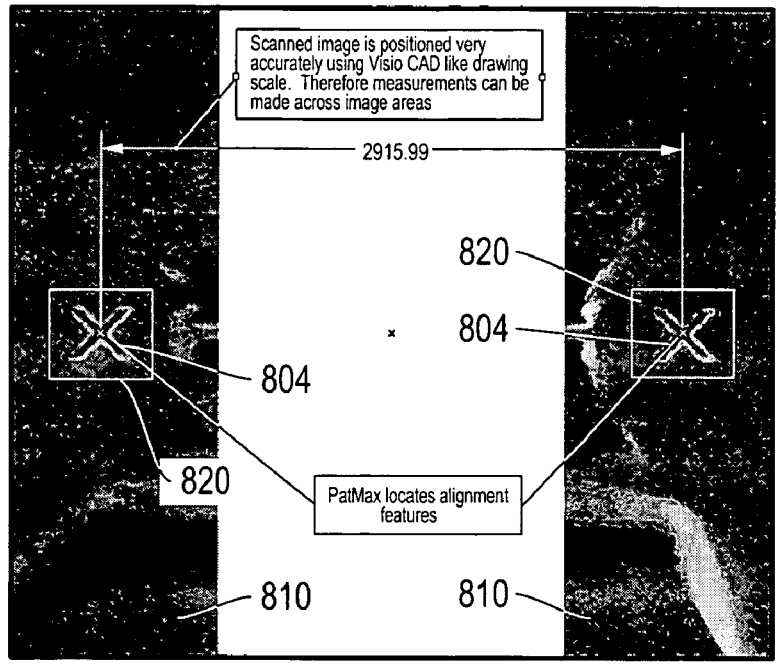
Figure 8D:
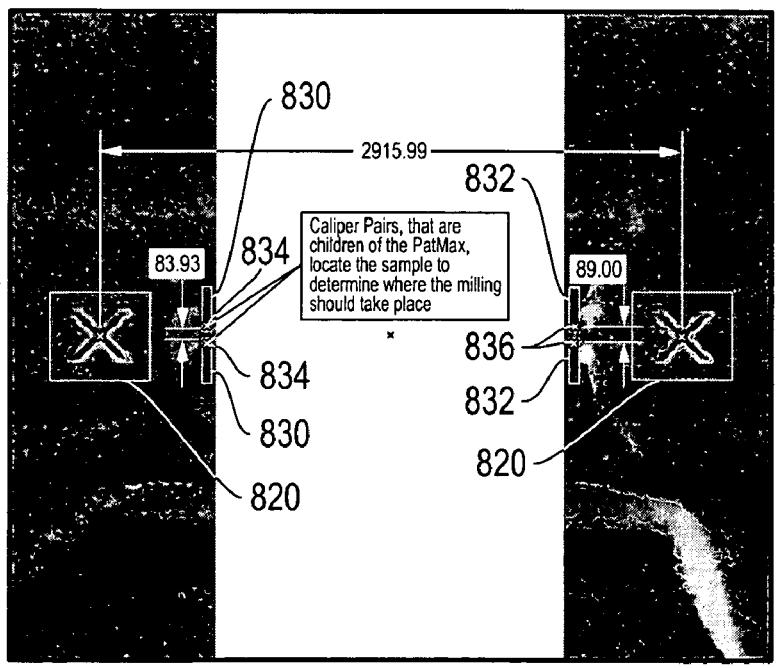

FIG. 8C shows that PatMax shapes 820 has located both of the reference marks 804. A dimension shape 822 is placed at connection points placed by the PatMax tool at the center of reference marks 804. Using the known image scale, dimension shape 822 determines the distance between the reference marks 804. Calipers 830 (FIG. 8D), which are child shapes of the corresponding PatMax shape, locate the edges of the sample area on one side of the sample, and a caliper pair 832 locates the edges of the sample area on the other side of the sample. Each of calipers 830 places a connection point 834 at the edge it detected and each of caliper 832 places a connection point 836 at the edge it detected.

Figure 8E:
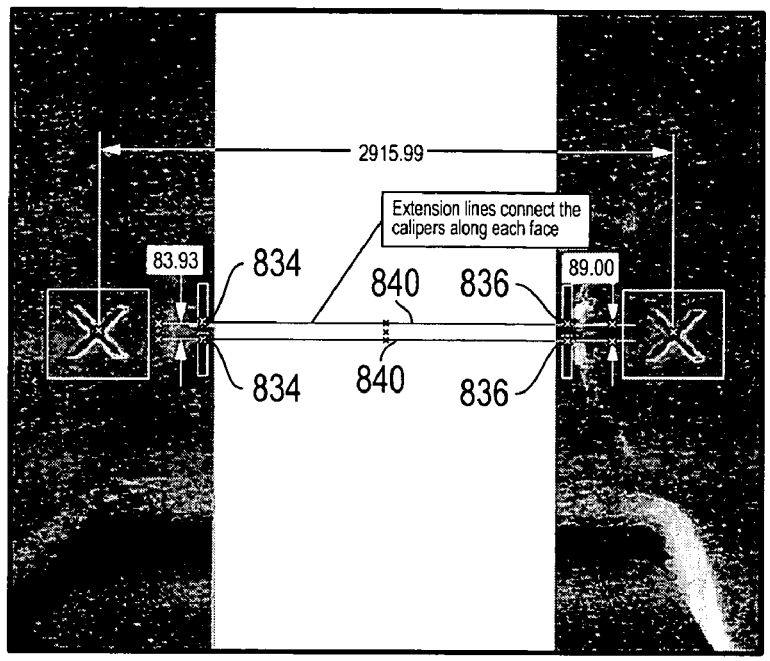
Figure 8F:
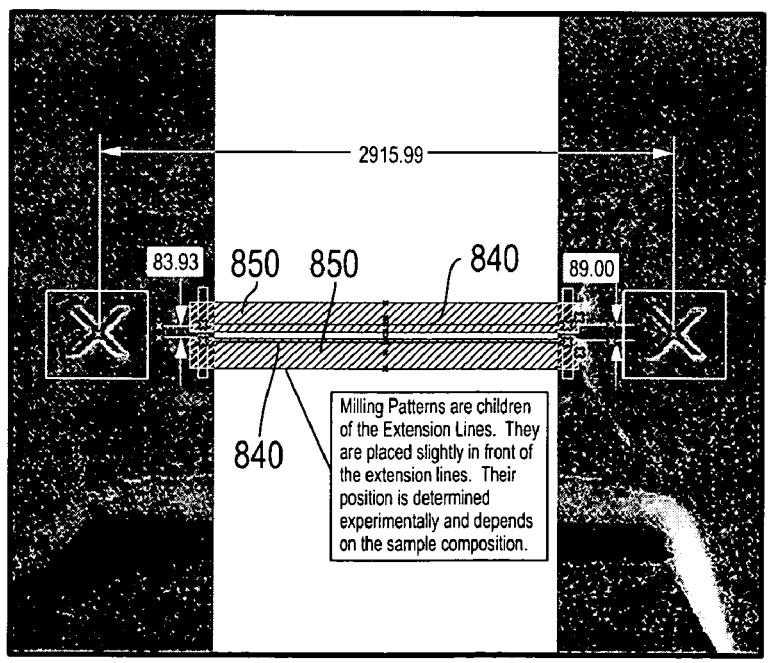

FIG. 8E shows that extension line shapes 840 are placed across the non-imaged area of the sample between the connection points place by the calipers at the sample edges. Line shapes 840 indicate the edges of the sample top without having to image the sample top. Lastly, milling pattern shapes 850 (FIG. 8F), each of which is a child pattern of the nearest extension line 840, are placed to indicate to the ion beam precisely where to mill in order to accurately mill the edges of the sample without milling the top. The exact placement of the milling pattern is determined experimentally and will depend upon the sample composition and the beam parameters. In some applications, the mill pattern shape slightly overlaps the extension lines. The milling pattern shape has associated code that instructs the ion beam to mill the pattern described.

Visio's integrated VBA provides the ability to automatically handle various aspects of the operation, such as Visio Documents including pages and shapes; Cognex VisioPro including the Cognex tool set; application specific items, such as manipulating cassettes, wafers, site lists, and adaptive sampling; machine interactions using machine specific libraries, such as FEI's xP system; bug fixes; workarounds; data logging; and spreadsheets for data presentation, trending, and charting.

The VBA behavior is associated with a Visio shape. The VBA code can be located in either a shape or a document. By associating the VBA behavior with a shape, the engineer can perform many functions, including setting the order of execution of the shape in the sequencer; adding a custom properties section to the shape's ShapeSheet and allow users to edit these properties using the Custom Properties dialog; saving the shape's configuration in the ShapeSheet when the Visio document is saved; altering the shape's behavior using ShapeSheet formulas; and testing the behavior by doubling clicking on the shape as described by EventDblClick.

When a user double clicks on a shape, the Sequencer will execute the function contained in the shape's EventDblClick cell. By default, this cell contains the OPENTEXTWIN function. This function opens the shape's text block so that the text can be edited when the user double clicks the mouse on the shape. The VBA programmer can place in the EventDblClick cell the name of the method of a custom behavior to be executed. The shape's/Behavior/DoubleClick/Run Macro menu provides the VBA programmer with a list of available macros that can be run for the shape. Typically, the function will be of the form ThisDocument.Run.

Once the VBA programmer has selected the appropriate function, the programmer can test the behavior by simply double clicking on the shape. In one embodiment, the sequencer is programmed to not execute the OPENTEXTWIN function because this function is the default function in any non-active, non-VBA shapes, and the function does not control anything outside of Visio. The sequencer will consult a registry based list of functions to ignore, although in some embodiments OPENTEXTWIN may be the only non-executable function.

VBA shapes will appear in the filtered list of active or VBA shapes in the sequencer tree. The user is able to start the sequence execution at active or VBA shapes. The VBA programmer can add a User.ActiveShape cell in the ShapeSheet of a VBA shape when creating it so the sequencer tree can identify it as a VBA shape.

Below, as an example of how the Visio shapes are connected to a physical devices, is a detailed explanation of the Move and Mill microscope shapes. Using these shapes as examples, skilled persons can create custom shapes for a variety of applications.

Figure 9:
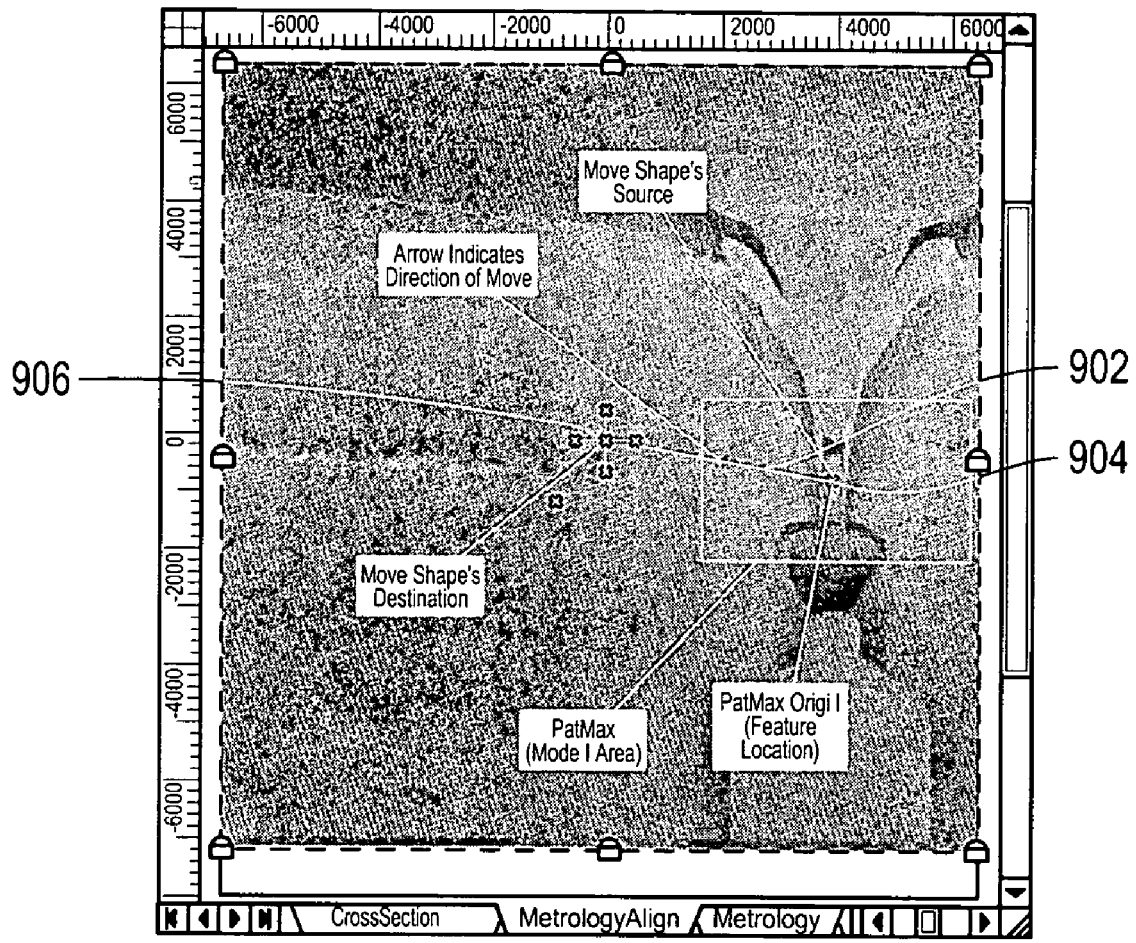
FIG. 9 illustrates a "Move" shape.

FIG. 9 illustrates the use of the Move shape. The Move shape is a composite shape comprising a Block Diagram/Basic Shapes/Cross shape and an Annotations/General-Connectors/Mid-arrow shape. To use the Move shape, the user connects a 1-D line 902 between the feature to be moved, such as a PatMax shape's origin 904, and the required destination, such as the X=0, Y=0 location at the center of the page, indicated by a crosshair shape 906. The Move shape's source location will vary depending upon the landing accuracy of the stage. The 1-D connection line 902 stretches to maintain the connection between the source 904 and destination 906. Selecting the Move shape will cause the configuration dialog to display, allowing the user to configure the move. Double clicking the shape will cause the move to execute.

To perform the move operation the Move shape has a link to the microscope. The software object that provides the microscope behavior is referred to as the Move object. The Move shape becomes part of the user interface of the Move object. The combination of the Move shape and Move object is referred to as the Move Tool. The Move Tool behavior should appear simple from the user's point of view. The user simply selects the destination and source.

The Move Tool preferably controls X, Y, and Z translations and stage rotation movements, allows relative and absolute moves; maintains electron and ion beam coincidence; maintains focus; and performs the move in the most efficient manner using a combination of beam shift and stage moves. The maximum amount of beam shift for each column must be configurable. The Move Tool also preferably employs Z corrections based upon a combination of a capacitance probe height measurement of the nose of the microscope and a height map; manages user units and an 'n' point alignment; manages an XY stage correction STACOM map, that is, a map of the non-linearities of the stage movement used for accurately positioning the stage; manages XY electron beam deviations due to stage and sample holder interactions; allows backlash to be configured for each axis; and manages two modes of capacitance probe usage depending upon the flatness of the wafer.

The move tool also preferably provides a means to retry the specified move a number of times if the move is unsuccessful and the microscope returns an error indicator, such as a "Stage Ready by Timeout" status. The move tools should also sample positions based upon cumulative stage position and beam shift and provide a diagnostic data including the Stage Ready by Timeout status and Cumulative stage distance traveled.

Another example of a microscope shape is the Mill shape, which causes a focused ion beam system to remove material from a work piece surface to expose, for example, an underlying layer or a cross section. In one embodiment, the user will design mill patterns using the PSConvert application (described below). The user may add a number of mill pattern masters to the milling stencil. The user can then drag these on to the page.

The milling pattern area and location is fixed by PSConvert, typically at X=0, Y=0. The user is allowed to change the location of the pattern by dragging the shape on the page. This pseudo movement will be achieved using beam shift. The vector area is dependent upon the horizontal field width (HFW) and the pattern's displayed vector area is therefore updated if the HFW is changed.

The configuration dialog is activated when the mill shape is created or selected. The configuration dialog will contain a series of tabs that allows the user to configure the column parameters, including aperture size, beam current, spot size, focus, stigmation, and high voltage and gas injection system parameters, including a gas name. Double clicking on the shape will cause the pattern to be milled after the user confirmation.

Another microscope tool is the image acquisition tool. The image provides the "wallpaper" that the user uses as a reference to place other shapes. The image function can be simplified if the image acquisition is separated from the image display. The image acquisition tool preferably allows the user to select which particle beam (ion or electron) or optical microscope to use for imaging. The user selects the beam or microscope by dragging an Ion, Electron or Optical shape off the stencil and onto a page. When the Image shape is dragged off the stencil onto the page, it preferably assumes the current xP image scan parameters and horizontal field of view. The image acquisition tool allows the user to set the horizontal field width (magnification), the scan parameters, the beam parameters, and the detector parameters. The user chooses the field of view, for example, by setting a scan area by setting the shape's width and height. The shape is a placeholder in the sequence, and the user changes the scan area via a dialog or by using an interface native to the imaging tool, such as FEI Company's UI1280 focused ion beam system interface, a manual graphical control interface, or even by using manual knobs on the machine.

Displaying images requires inserting an image control into the page. This can be performed using the Microsoft Forms 2.0 Frame control. The required functionality can be achieved by inserting the Frame control into a Visio Background Page. Using a background page has the added advantage that the user does not accidentally select the shape but because only one background page is required for the whole document, this technique limits the page to a single image.

The page's scale can be set using the image pixels per micron property. The image aspect ratio can be determined by the active beam and stage tilt. Typically, the frame will be standard xP 512*442 aspect ratio. Each Image shape will require the a new Visio page since the page scale must be set to match the xP HFW. One can use discrete X and Y page scales to take into account any possible image tilt.

The user is then free to change the HFW using the manual user interface (MUIF) knob; any change will cause the page scale to update. The user is also free to resize the page, effectively creating a selected area scan. If the user changes the scan area then the xP HFW will be adjusted. This requires careful calculations to ensure that legal HFW values are set for the active column.

If the user reduces the HFW, the wallpaper image will be cropped and zoomed to fit the new image size. If the HFW is increased, the wallpaper imaged will be zoomed out and centered to fit the new image size, causing a blank area to be displayed around the image.

The configuration dialog is activated when the image shape is created or selected. The configuration dialog will contain a series of tabs that allows the user to configure the following: scan parameters, including image size, image resolution, and pixel dwell; column parameters, including aperture, beam current, spot size, focus, stigmation, and high voltage; and detector parameters: detector, bias, grid, contrast, and brightness.

After the image shape is configured, double clicking on it will cause it to grab an image frame. Once the user is satisfied with the configuration of the scan area and HFW, the shape should have all of its protection enabled. This prevents the user from mistakenly moving the image shape by accident when attempting to manipulate other shapes that are over the image.

The execution order is split into two hierarchies: the page order and the order of shapes within a page. It is preferable to execute the pages in order, since Visio allows the user to reorder the pages by right clicking on the page tabs. Therefore, each page just needs its own list control specifying the run order for shapes within the page. This can be a simple docked window containing a list of shapes. Since the page is essentially a collection of shapes, the shape sequence data is preferable stored inside the page ShapeSheet.

Figure 10:
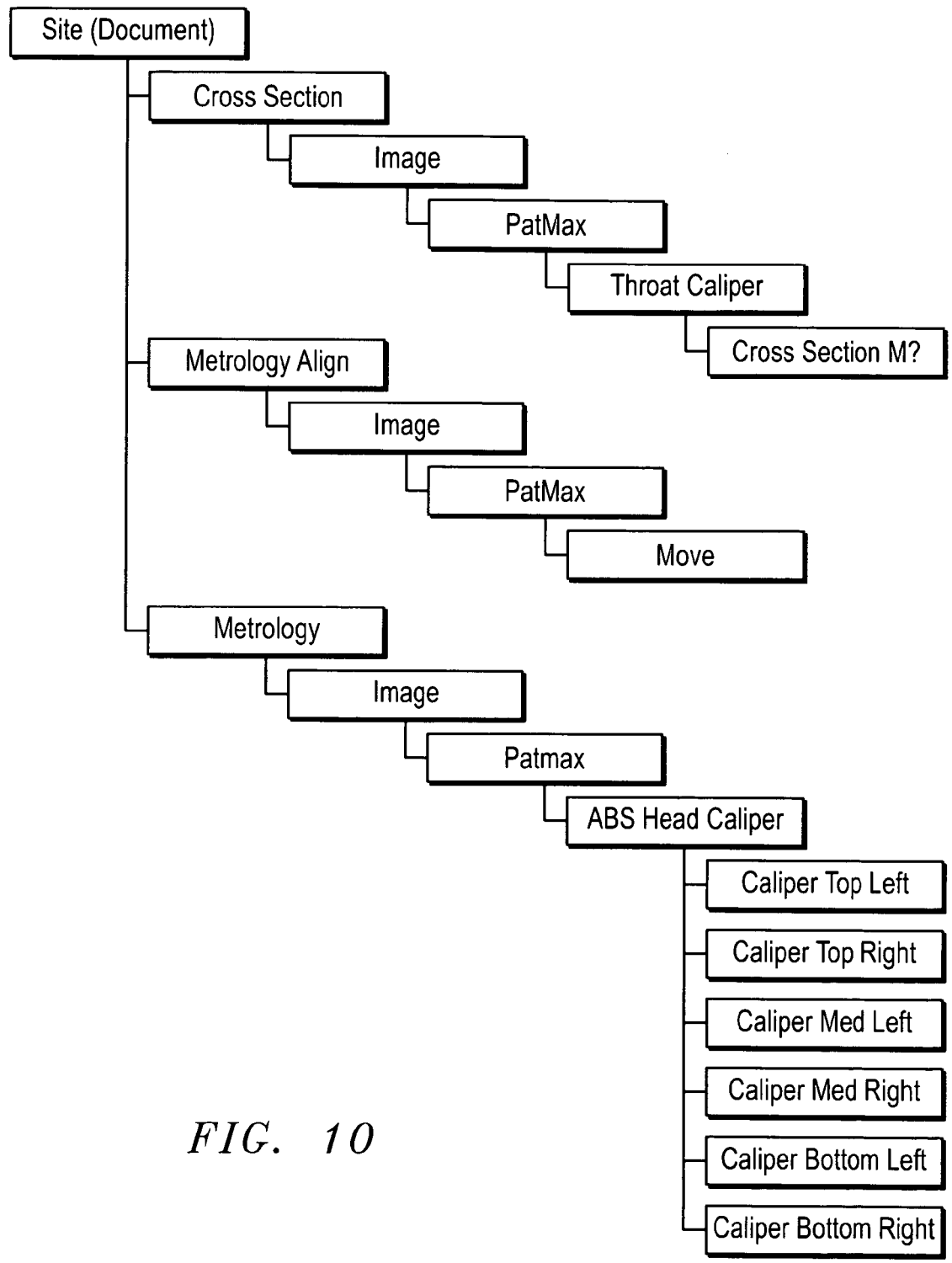
FIG. 10 illustrates a typical sequence of execution of operations in an embodiment of the invention.

The entire run order of the shapes within a page can be ascertained by iterating through each shape. FIG. 10 shows the run order of a typical ABS head metrology application.

The custom properties, data, events, and methods available in Visio useful in implementing the invention. Visio shapes can be used to store non-visual information, for example a PatMax contrast threshold. Visio provides a number of features for storing additional data. These include the three miscellaneous data members Shape.Data1, Shape.Data2, and Shape.Data3 object properties, referred to collectively as Shape.Data1/2/3. These three members appear to have a capacity of at least 64 K of text. The Data1/2/3 members provide convenient storage for any custom (non-Visio) XML data associated with the shapes, for example, Cognex persistence data. Associating custom data with shapes is very useful because when a shape is duplicated or copied, the custom data is also copied. Visio shapes can also be linked to database records in various ways using the Database Wizard Addon.

Visio also provides for storing information in the Custom Properties, User and Scratch areas of the ShapeSheet. The Visio ShapeSheet allows the user to add "User" fields to any of the ShapeSheet sections.

It is possible to store configuration data in an XML format in the Shape.Data1/2/3 fields. The Cognex VisionPro PatMax and Caliper tools support XML serialization methods. Cognex designed their serialization methods using the CogFile objects Load and Save methods. Instead of using files, it is preferable to use the shape's DATA1 property as a serialization target because when shapes are copied, their DATA1 contents are also copied. Saving the Visio document will of course save the contents of DATA1. Therefore a Master shape can be configured with default custom data at install time and this data will be copied when the shapes are dragged off the stencil.

PatMax and Caliper XML data can be saved using the shape's DATA1 property, for example, by using statements such as:

mShape.Data1=CogMisc.SaveObjectToString(PMTool, cogPersistOptionAll—cogPersistOptionInputimages—cogPersistOptionOutputimages, cogPersistFormatXMLWithLineBreaks)

and data can be loaded using a statement such as:

Set PMTool=CogMisc.LoadObjectFrom String(mShape.Data1, cogPersistOptionAll)

Executable code can be added to Templates, Documents, Stencils, or ActiveX Controls. One embodiment uses ActiveX Controls as the main location for automation behavior.

A basic implementation may contain thirty or so basic shapes. Over half of these are typically Dimension shapes that require very few modifications to their original Visio behavior. By copying and modifying these simple shapes, users can build several hundred or possibly thousands of combinations of complex shapes. Therefore, it is preferred to put as little code into the shapes as possible, so that installing a new version of the software is as simple as possible.

The use of ActiveX Controls makes updating an existing installation more straightforward since when copying the master stencils to make new masters, only the spreadsheet data will be copied, not the additional shape code associated with the shape.

Some form of control is required to execute the prescribed behavior when the user performs some action on a shape. Visio splits user actions into two discrete methodologies: ShapeSheet events and Visio application events.

The events section in a shape's ShapeSheet has cells that specify the function calls that are to be made when the following events occur. ShapeSheet events include EventDblClick, which occurs when the shape is double clicked; EventDrop, which occurs when the shape is dropped onto the drawing page; and eventXFMod, which occurs when a shape's orientation or position on the page is modified. EventDrop is useful for creating and configuring objects, such as a Mill object, when the corresponding shape is dropped onto the spreadsheet. EventXFMod is useful, for example, for defining passive shapes, and EventDblClick is useful for executing the action associated with the shape.

ShapeSheet events are used to handle single shape events. These events are handled by using a CALLTHIS or RUNADDON command as the content in the cell indicating the event handler. These events allow automation without writing Visual Basic event handling. Because some functions require VB event handling, ShapeSheet events are not really an advantage. Some events like EventDblClick are only available in the ShapeSheet, others like EventDrop are available via the Visio Application ShapeAdded event.

Visio application events that relate to shapes handle single or multiple shape events. Visio Application events provide common event handlers for instances of each type without the extra effort required to configure a ShapeSheet event cells. With these common events, Visio document, page and shape managers can be designed.

The ShapeAdded event is triggered after one or more shapes are added to a Visio document, and the SelectionAdded event is called once for additions of multiple shapes. The ShapeChanged event occurs after a property of a shape that is not stored in a cell is changed in a Visio document. The SelectionChanged is called once for multiple shape selections. This event is useful in certain circumstances when a shape is moved, such as the movement of a 2-D shape within a group or the movement of a connection point of a 1-D shape. The ShapeParentChanged event occurs after shapes are grouped or a set of shapes is ungrouped. It is useful for redrawing execution hierarchy diagrams. The BeforeShapeDelete event occurs before a shape is deleted, and the BeforeSelectionDelete is called once for multiple selections. These events are useful for deleting shapes and redrawing shape hierarchy diagrams. The BeforeDocumentSave/As event occurs just before a Visio document is saved and is useful for saving FEI object data to shape DATA1 Cell.

Many other events are documented in Visio and skilled persons will be able to select appropriate events applicable to specific implementation. For example, the DocumentOpened event occurs after a Visio document is opened and is useful for drawing shape hierarchy diagrams. The PageAdded event occurs after a page is added to Visio document and is useful for redrawing shape hierarchy diagrams. The PageChanged event occurs after the name of a page, the background page associated with a page, or the page type (foreground or background) changes and is useful for redrawing shape hierarchy diagrams. The NoEventsPending event occurs after the Microsoft Visio instance flushes its event queue and is useful for initiating the refresh of results spreadsheets when shapes have completed all geometry changes. Shapes receiving a ShapeChanged event should set a "dirty" flag. The NoEventsPending handler can query "dirty" flags and act appropriately. The WindowTurnedToPage event that occurs after a window shows a different page and is useful for redrawing shape hierarchy diagrams.

Cognex uses the term "tool" to describe the behavior object that performs the action of searching. Cognex uses the term "control" to describe the ActiveX Control that the user uses to configure the tool. Visio use the term "shape" to describe the object dragged from the stencil and placed upon the shape. FEI uses the term Gizmo to describe the combination of shape, tool and control.

A Gizmo will comprise the following objects: an object having geometric properties, such as a Visio shape, a software control, such as an ActiveX Configuration Control, and a tool object, such as a vision tool or machine interface. The Gizmo is a COM object engineered by FEI to wrap a FEI or third party component, such as a Cognex PatMax tool, and associate it with a Visio shape. The Cognex PatMax tool comprises a CogPMAlignTool object containing behavior logic and a CogPMAlignCtl ActiveX Control to allow the user to configure the behavior logic. The shape's ShapeSheet will contain a User.Gizmold Cell indicating the type of the shape. A collection of Gizmolds and their associated Gizmo Progid's will be maintained in the registry. A Gizmo can be thought of as a wrapper that converts a third party "Tool" interface to a generic interface that the GizmoManager can handle.

Additional Gizmos can be installed without re-installing the program. Applications engineers can write VBA code modules and associate the module with a shape on the stencil. These are called "Custom Gizmos." Custom Gizmos will allow applications engineers to create additional data logging and system workaround tools. The VBA code should be associated with the Stencil.

The GizmoManager can use the Visio BeforeDocumentSave event handler as a trigger to serialize the CogPMAlignCtl data into the shape's DATA1 property. Since the whole Visio document is being saved, the BeforeDocumentSave event handler will have to iterate through the entire Gimzo Collection, serializing all the Gizmos' data into their associated shape's DATA1 properties.

Gizmos are managed by a GizmoManager, which is a Visio AddOn engineered to manage the interactions of the user and the sequencer with Gizmos. The GizmoManager supplies an interface having the following methods: initialization, run, save, and delete; the following properties: Shape, ResultsSheet, Type, 1D; and the following events: PreRun and PostRun, including Success/Failure Status. The GizmoManager is general driven by Visio Events, push buttons, and menus calling its methods.

Figure 11:
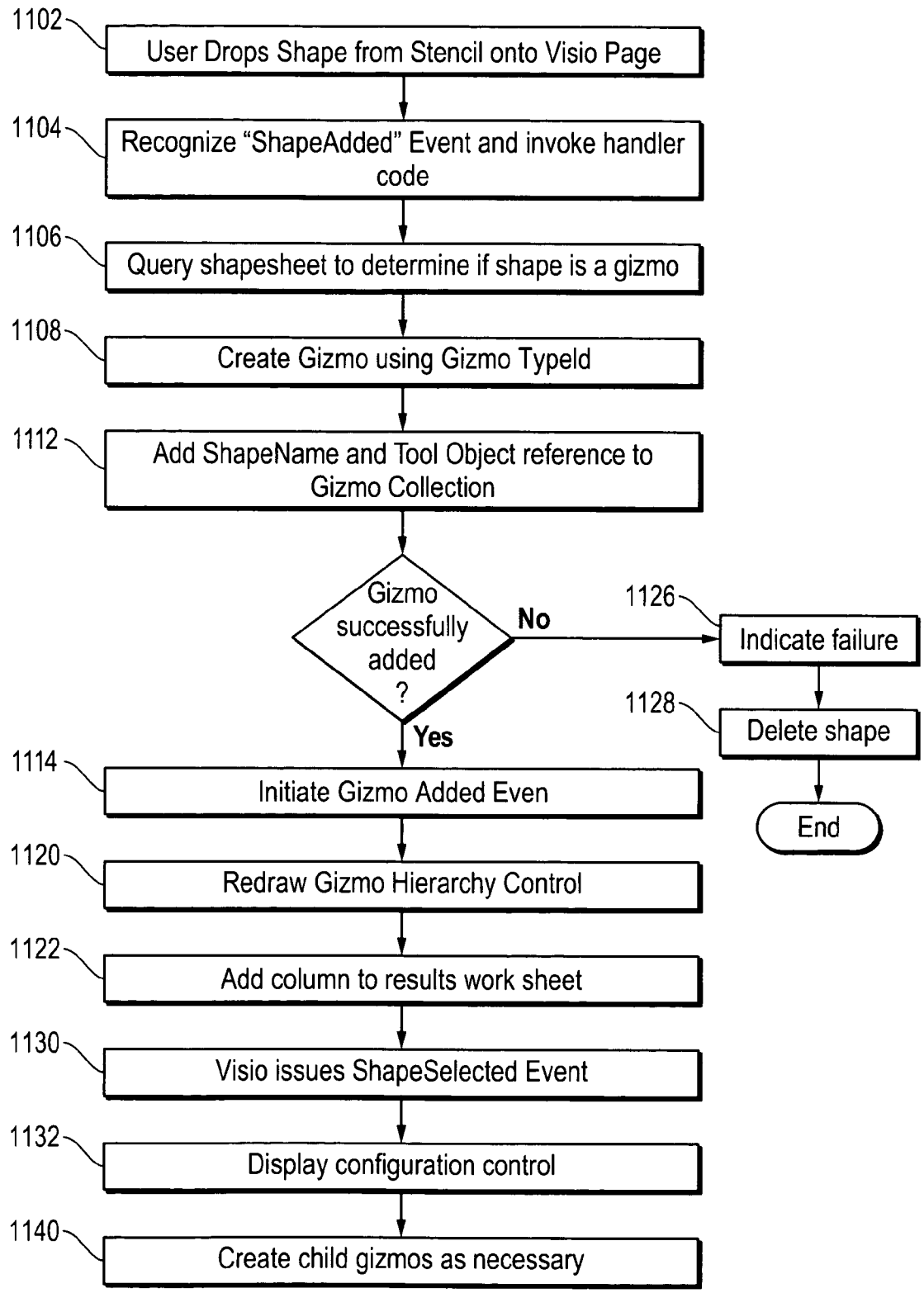
FIG. 11 shows some of the actions that occur when a user adds a shape to a drawings in one embodiment of the invention.

FIG. 11 shows the sequence of events that occur when the user drags a shape on to a page and a Gizmo is instantiated. In step 1102, a user drags a shape off a stencil on to a Visio page. In step 1104, Visio recognizes that a ShapeAdded event has occurred and is directed to the event handling code. In step 1106, GizmoManager's ShapeAdded event handler determines if the shape is a Gizmo by interrogating the shape's ShapeSheet User Section for the User.GizmoTypeID. If the User Cell exists, the GizmoManager attempts in step 1108 to create an instance of the Gizmo by using the GizmoTypeID to iterate through a collection of installed Gizmos. If the Gizmo is created successfully, the GizmoManager interrogates in step 1110 the shape's DATA1 property. DATA1 will contain any 11 ML data that will be used to configure the Gizmo using the Load Method. The majority of the XML data will be the tool object's configuration.

In step 1112, the GizmoManager adds the ShapeName and Tool object reference to the Gizmo Collection. At this point, the user may be prompted to change the name of the shape to something fitting like PMTool.SiteAlign. If the Gimzo is created successfully, in step 1114 a GizmoAdded event is fired, which causes Gizmo Hierarchy Control to be redrawn in step 1120 to show the new shape in relation to other shapes in the page and GizmoManger adds columns to the results worksheet in step 1122. If the Gizmo is invalid, a dialog is displayed indicating to the user in step 1126 that the Gizmo is not installed correctly with the reason for failure. Upon closing the dialog, the shape is deleted in step 1128.

Since the shape is now selected on the page, Visio should issue a ShapeSelected event in step 1130. The GimzoManager's ShapeSelected event handler will use this as a trigger to display the Configuration Control in the AddOn Window in step 1132. Because Visio only sends one ShapeAdded event even if a composite shape master is added, the GizmoManager's ShapeAdded event handler must iterate in step 1140 through the Visio shape object supplied by the ShapeAdded event, creating the necessary Gimzos for the child shapes. Typically, child shapes will have fitting names already specified on the stencil.

Figure 12:
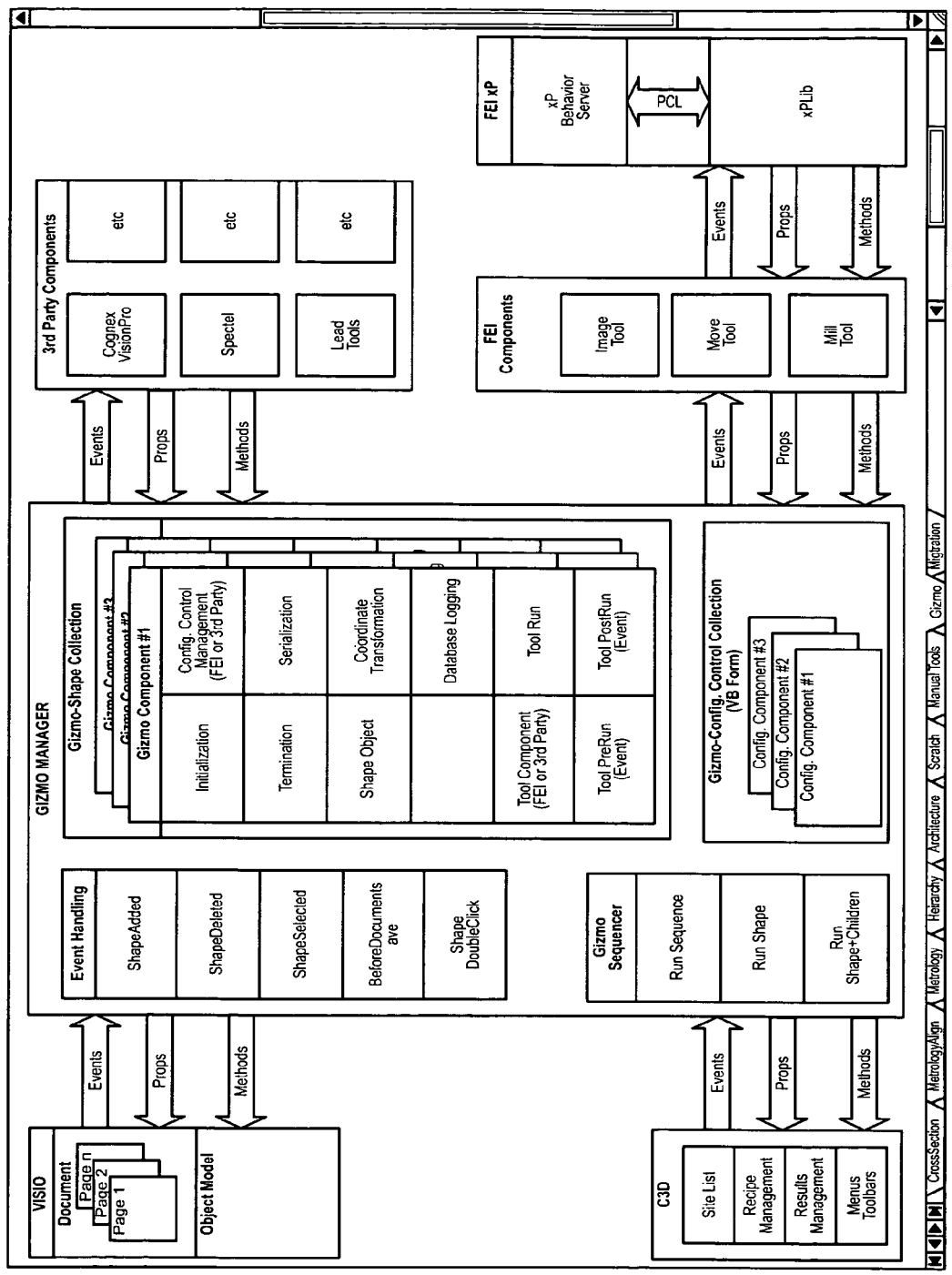
FIG. 12 is a block diagram showing the structure of a Gizmo manager and how it interacts with other components.

FIG. 12 is a diagram showing the functional blocks of a GizmoManager and the flow of information between the blocks.

The Gizmo manger controls the events that occur when the user performs certain actions on FEI shapes. The following table shows typical reactions of the GizmoManager on shapes, actions and events.

| User Action on Shape (Event) | Gizmo's Reaction (Behavior) |
| --- | --- |
| Drop, Open Document, Duplicate | Creates an associated Gizmo, Gizmo creates a tool populated with the shape's XML data from DATA1 cell. Etc. |
| Select | Shows the Configuration Control |
| Deselect | Hides the Configuration Control |
| Moved or Resized | Changes the shapes XY location |
| Group, Ungroup | Defines the shape's group behavior |
| DoubleClick | Executes the Gizmo's, Tool's Run method |
| Delete, Close Document | Destroys the associated Gizmo |
| Save Document | Serializes the Gizmo's data into XML data into the shape's DATA1 cell |

An example of a Gizmo is PMTool, which is based upon a tool from Cognex VisionPro software. The Gizmo comprises the following: a Visio shape, an ActiveX Configuration Control, and a Tool object.

Visio provides the shape, which is just a rectangle with a connection point at width*0.5 and height*0.5. VisionPro provides the configuration control, CogPMAlignCtl and the behavior COM object, CogPMAlignTool. The Visio shape is used to train the CogPMAlignTool. The CogPMAlignTool's region of interest is set by the Visio shape's area. For simplicity, the pattern origin is fixed in the center of the region of interest. The connection point could also be used to define the pattern origin to allow the user to move the connection point.

The data from one shape appears on the shape on Visio page, on the Title bar of the configuration dialog, on several columns in the data-logging worksheet, and on a branch in the sequence tree. Therefore, it is preferred that the shape be given a name to identify it. The user will be prompted to name the shape when it is first dropped on to the Visio page. The user can choose to use the default name provided by Visio, for example, PMTool.3, but renaming the shapes to a more descriptive name like PMTool.SiteAlignment makes the recipe more maintainable.

Since xP, Visio and VisionPro have different coordinate systems, some coordinate transformation is necessary. xP uses an origin in the center of the field of view, Visio uses the lower left and Vision Pro uses the upper left. For ease of programming the xP coordinate system is preferred and coordinate system conversion is quite straight forward. Visio provides a LOCTOLOC command that can be used to convert the coordinate space of a given shape to that of another shape on the page or the page itself.

The following formula converts the X axis center of a shape to the center of the page:

(PNTX(LOCTOLOC(PNT(LocPinX,LocPinY), Height,ThePage!PageHeight))—(ThePage!PageWidth*0.5))

The scale of the page is set is accordance with the pixels per micron of the image. Visio also provides an ANGLETOLOC command that can be used to convert the angle of a given shape to that of another shape on the page or the page itself.

ANGLETOLOC(Angle,ThePage!PageWidth,ThePage!PageWidth)

The following code converts the image pixels from VisionPro to centered microns:

Dim t As New CogTransform2DLinear

'Skew by PI, Offset by Image Width/2 and Height/2 to align Vx Coords to xP Coords was 96/25.4 t.SetScalingAspectRotationSkewTranslation ImagePixelsPerNanometer, 1, 0, PI, IDBTool.OutputImage.Width/2, IDBTool.OutputImage.Height/2

The following code transforms the scale from pixels to nanometers:

IDBTool.OutputImage.CoordinateSpaceTree.AddSpace "/", "nm", t

IDBTool.OutputImage.SelectedSpaceName="nm"

The Image Tool is responsible for loading the image data into the VisionPro image database object, or whatever object is decided on.

The PreRun, Run, PostRun and Configuration Dialog Activation is implemented so that it can function for tool configuration and testing and for running the tool as a part of the sequence. The user will configure the tool using the CogPMAlignCtl. This control has a run button located on its tool bar. The user will use the run button to test the configuration after training. The run button calls the run method. The run method can also be called by the sequencer.

The PreRun, Run, PostRun dialog activations are all executed as a result of calling the Run method. This is completely compatible with run button on the CogPMAlignCtl. CogPMAlignTool does not quite provide all of the functionality required for may embodiments of the invention. The coordinate system transformation and the output of the run time results to the database necessitates some additional behavior. Therefore, a FEIPMAlignTool object is preferably created with the following behavior:

Before the actual run method is called, the control fires a PreRun event to allow any pre run code to be executed first. PreRun coordinates the conversion from Visio to VisionPro and is required at training time. The user can preferably set a search area of the CogPMAlignTool. Running the method calls the CogPMAlignTool run method and requires encapsulating CogPMAlign for training, running, results, etc. After the run method is complete, VisionPro fires a PostRun event. The post run operation will coordinate conversion from VisionPro to Visio to transform search results to position the associated Visio shape and to output data to the logging worksheet. This code will move the Visio shape to the search XY location for the current image and will send the tools' results to the logging worksheet.

When the user selects an FEI type shape, the associated configuration dialog will be displayed. The CogPMAlignTool has a ControlProgID property. This data can be used to create a CogPMAlignCtl and add it to the collection in the configuration form. The subject of the CogPMAlignCtl must be set to instance of the CogPMAlignTool.

The CogPMAlignCtl is preferably modified to remove some of the unwanted features. Modifying the control is completely acceptable since Cognex provides the VB source code.

A Visio document contains the complete site operation for the recipe. These operations will be spread across a number of pages. Each page will define an image based upon beam, magnification and tilt. The operation for the page will be with respect to the image beam, magnification and tilt. The order of the pages in the Visio document defines the order in which each page will be executed. The user may reorder the pages. Reordering is already provided as a Visio function. The Parent/Child hierarchy of the shapes on a page will set the execution order. The user may reorder shapes of the same hierarchical level, thus preserving the Parent/Child relationships. The user may drag child shapes into and out of parent relationships. The Visio document structure will provide the input data for the sequencer.

A "Sequence Explorer" tree display, similar to Visio's Drawing Explorer. It will preferably provide a visual representation of the run order and hierarchy of the pages and shapes and allow the user to reorder the shape and page execution order. Reordering will required updating the Visio document structure. Clicking nodes in the tree will activate the associated page and shape. Activating the shape will display the shape's tool configuration dialog. The tree will be constructed using the Visio document structure. Since the Visio document provides the input data to the sequencer, a data collection is required to associate a shape name with a Configuration Control (dialog) and a Behavior object (few lines of xPLib code). The Sequence Explorer functionality can be provided by Visio's Drawing Explorer. The Drawing Explorer does not provide the ability to reorder shapes or pages. Pages can be reordered using Visio's Page Tabs.

The Configuration Controls are preferably housed on a single form whose parent window will be a Visio Window. The configuration control can be a Visio visAnchorBarAddon, whose parent will be the Visio Page, or a visDrawingAddon, whose parent will be the Visio MDI frame.

Only one configuration control type instance will be created regardless of how many shapes of the same type are in the active document. The AddOn window will contain a blank VB form. The shape Manager will use the Visio ShapeAdded event handler to iterate through the ControlForm controls collection to determine if a new type of configuration control should be created and added to the control collection. The configuration controls preferably follow the Cognex VisionPro model where the Subject property of the control is set to the behavior object instance when the associated shape is activated by the user. The shape Manager will use the Visio SelectionAdded event handler to determine which control to make visible and hide all of the others. This assumes that Visio fires the ShapeAdded event before the ShapeSelected event.

Only one type of configuration control will be active at a time. If the user selects multiple shapes of differing types, the AddOn window will display a blank form indicating that "No Common Properties" exist. This is in-line with the Visio Shape Size&Position Dialog behavior.

If the user selects multiple shapes of the same type, the configuration control's Subject will be set to that of the first shape in the selection collection. Any of the properties changed will be applied to all of the Behavior Objects of all of the shapes in the Selection Collection. This is in-line with the Visio Shape Size&Position Dialog behavior. This includes the shape Region of Interest.

Once created, by selecting a shape, the AddOn window will always be visible. When no shapes are selected, a blank form indicating that "No Selection" exists. If the AddOn window type is a visAnchorBarAddon the user can close it. If the window is a visDrawingAddon it cannot be closed.

Data developed by a Gizmo is directed to an embedded spreadsheet/worksheet. Each FEI Gizmo will have a configuration tab to allow the user to specify which data should be directed to which worksheet.

Typically, metrology dimensions derived from the dimension shapes will be directed to the Results Worksheet by default, although the user will be able to specify alternative worksheets. Other Gizmos, such as PatMax and Move have data that is considered diagnostic. Non-dimension Gizmos will typically have their own worksheet.

The Gizmo manager is preferably smart enough to deal with shapes' custom properties. Custom properties give the applications engineer a method of easily providing data entry controls for their custom shapes. The EditControls for each Gizmo has a blank tab that can be used to dock the Visio custom properties dialog. The Gizmo manager determines whether the selected shape has a Custom Properties section and docks the Custom Properties dialog onto the EditControl tab.

Because of the rapidly changing nature of the semiconductor industry, it is impossibly to precisely predict future metrology requirements. It is therefore desirable for graphical metrology to build a collection of primitive Gizmos, whose Visio shapes can be joined together by either applications engineers or customer metrology engineers, using either grouping or connections, to produce complex (or composite) metrology Gizmos. This approach avoids the need for software engineers to write software for numerous custom Gizmos to perform complex metrology.

Therefore metrology Gizmos preferably provide the flexibility of scripting combined with the ease of use of Visio. At most, FEI applications engineers and customer metrology engineers will have to write Visio ShapeSheet formulas to join together the primitive shapes and construct the complex metrology shapes required. Once constructed, these complex shapes can be placed on a Visio stencil.

Metrology Gizmos preferably include the flexibility of scripting combined with the ease of use of Visio. At most, FEI applications engineers and customer metrology engineers will have to write Visio ShapeSheet formulas to join together the primitive shapes to construct the complex metrology shapes required. Once constructed, these complex shapes can be placed on a Visio stencil.

Some embodiments use helper shapes to join other shapes. Helper shapes have only a Visio run time behavior, they do not have an associated Gizmo. They do not perform image processing, dimensioning or microscope functions, and they do not have an EditControl, although they may have Visio Custom Properties. Their only function is to join together active shapes like calipers. Helper shapes are primarily just geometric shapes.

A Stigmation Map can be used for the SEM image stigmation and focus distortion that is induced by the magnetic disturbance between the electron column, the wafer and the stage at various locations on the wafer.

To ensure recipe independence between systems, two maps may be required. A system dependent map that corrects for the individual machine and a product dependent map that corrects for individual product type. A system dependent map that is unique to each individual microscope is adequate for most applications. But as feature sizes shrink and the industry demands higher image quality, a product dependant map is preferred. The two maps are usually summed to provide X and Y stigmation values and a working distance value at wafer locations determine by bounding X and Y locations on the wafer.

Visio.VSD documents may contain shape-related Gizmos to set correction values such as SEM stigmation and working distance. Flexibility to apply the mapped values is preferred. The most flexible method to apply the stigmation values is to allow the application programmer to reference the mapped values in the SEM Image Gizmo Configuration Control (FeiSEMImageEditCtl). The stigmation and working distance values can be referenced by ShapeSheet cell formulas that allow the application programmer to combine the machine and product dependant values for the current site. The microscope is then set to these values before the image is acquired.

The FeiSEMImageEditCtl will have a checkbox that is similar to the Visio ShapeSheet and will allow the applications engineer to view either a formula or result (value). There may actually be times when the applications engineer wishes to apply a fixed stigmation value. In this case, the user can just enter a number or record the value from the microscope.

The same magnetic disturbance that affects the electron column's stigmation and working distance also affects the position of the electron beam. This causes a loss of coincidence between the ion beam and the electron beam. Coincidence errors of up to 20 microns have been reported. The coincidence map provides the X and Y distance that the stage must be moved when the primary beam is switched from Ion to Electron.

Because it is not intuitive for the application programmer to place or move a Gizmo in the execution sequence just because the primary column is changed, the SEM Image Gizmo preferably applies the correction factor by making a stage move, but only if the primary beam is not currently the Electron beam. The actual correction values will be applied in a similar manner to the stigmation map whereby the applications programmer determines an algorithm for calculating the correction value by combining system correction and the product correction.

A preferred embodiment provides a map editor to allow the applications engineer to view the map data. The syntax of error reporting should allow for efficiently tracking down map data format errors.

The product dependant map files are properties of the recipe and are packaged in the recipe archive files. Product dependant map files travel with the recipe. Their implementation is quite straightforward.

System dependant map files reside on the system. When only one map of each type is required, the filenames of the coincidence and stigmation map can be specified in the registry. Sometimes, however, multiple maps of each type are required, for example a stigmation map's correction is only valid for one stage rotation angle. If the recipe specifies two passes, with each one at a different rotation angle, two stigmation maps will be required. The stigmation maps for each pass cannot simply be specified for each pass in the registry, because different recipes may have different rotation angles for a given pass number and therefore require different maps. Therefore, the system map filenames must be specified in the recipe.

When GEM is enabled, the GEM Host can download a table of supplemental variables for each wafer in the lot. The values are formatted as double length floating point (double).

An example use case of supplemental variables would be as follows:—

In a data storage FAB, the placement of a given feature is determined by the individual system used to perform a previous process step. For example, a stepper system may have an inherent offset that is known to the host programmer. The host programmer can communicate the XY offset in a pair of supplemental variables to the metrology system. The application programmer can apply this XY offset to a milling location.

The supplemental variables are also a type of process correction input and therefore will be displayed in the same manner as maps in a worksheet and also as a single branch in the recipe tree. The supplemental variables values will be written to predefined user cells in each page of the recipe's .vsd files for both process and alignment.

At run time model area shape should scale to enclose an area on the image that represents the feature. This would be a useful feature to give the user confidence that the Gizmo has located the feature and measured its approximate size. The scale feature should also be applied to the model origin shape since the user may want to scale any child objects with respect to the size of the located feature.

Results of execution of shapes are preferably saved in a format for data analysis, such as a spreadsheet, to calculate user specified statistics as each site is processed. An embodiment may optionally include feature adaptive sampling, where future site locations are calculated by user developed formulas that use the results of previous sites. Adaptive Sampling is described later in this document.

The end user may configure the appearance of the run time display by assigning shapes to layers to assist in organizing shapes. The user may set whether a particular shape is printable or not. Typically, dimension shapes will be printable, while active and VBA shapes will be non-printable. The user may of course change the shape's color, line style and fill pattern and add text. Visio documents can be inserted as objects in a Word document, but because of the document size, it is more useful to save a page in a variety of image formats, such as bitmaps, TIFF, or JPEG.

In some embodiments, the tree sequencer can be replaced with a Visio flow chart. Two views of the tools would define the operation. The physical view would be the XY position of the tool with respect to the image, the tool's children and other tools. The logical view would determine the execution sequence based upon each tool's run time Boolean evaluation. The evaluation could be as simple as a pass/fail tool execution status, a fixed for-next expression used to provide repeating of one of more shapes, or a more complex VBA while-do, or do-until expression. Example of complex sequences could be pattern recognition used as in an ion beam mill end-point-detection scenario. A Visio document is defined to describe the entire sequence of operation at a given site of interest. A "Document" can consist of multiple pages. A single page could contain the metrology configuration. The page is the canvas to design the metrology configuration.

Flow-chart programming, or conditional branching provides an additional level of automation, control and recovery. For example, in milling to re-expose an alignment mark or fiducial covered during a manufacturing process, it is desirable to stop the milling process as early as the fiducial is observable. Using conditional branching available with flow chart programming, it is possible to continuously monitor the optical image and when the pattern recognition identifies the complete target, it would cease milling. A system of conditional branching would also be able to respond to situations such as a misplaced mill that caused partial exposure and rework the damaged area. Conditional branching can also be used to make decisions about a feature that would lead to classification or appropriate methods of site preparations. For example, the axis could be identified so the defect could be cross-sectioned appropriately.

Figure 13:
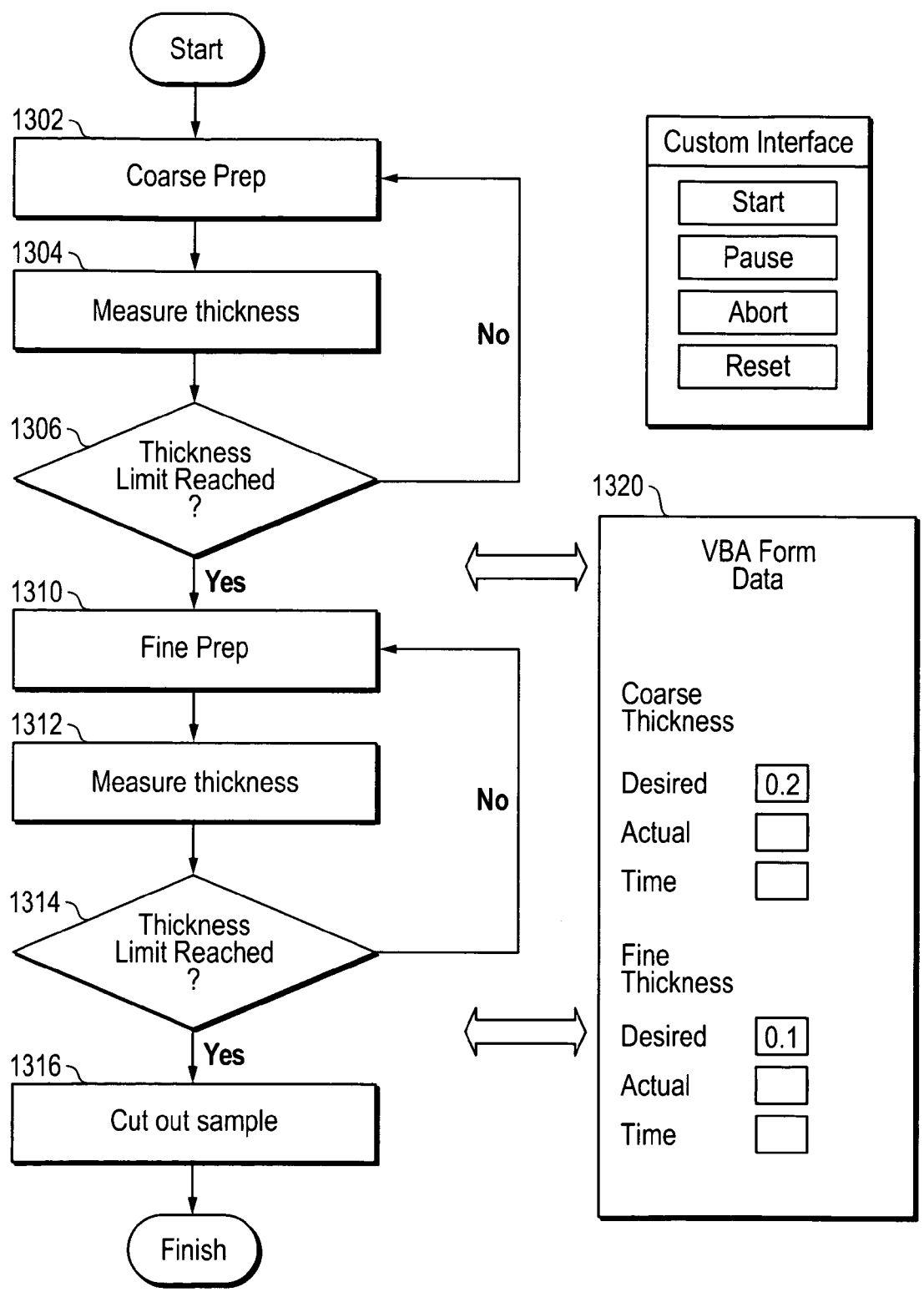
FIG. 13 is an example of a flow chart used to program the operation of a tool.
Figure 1:
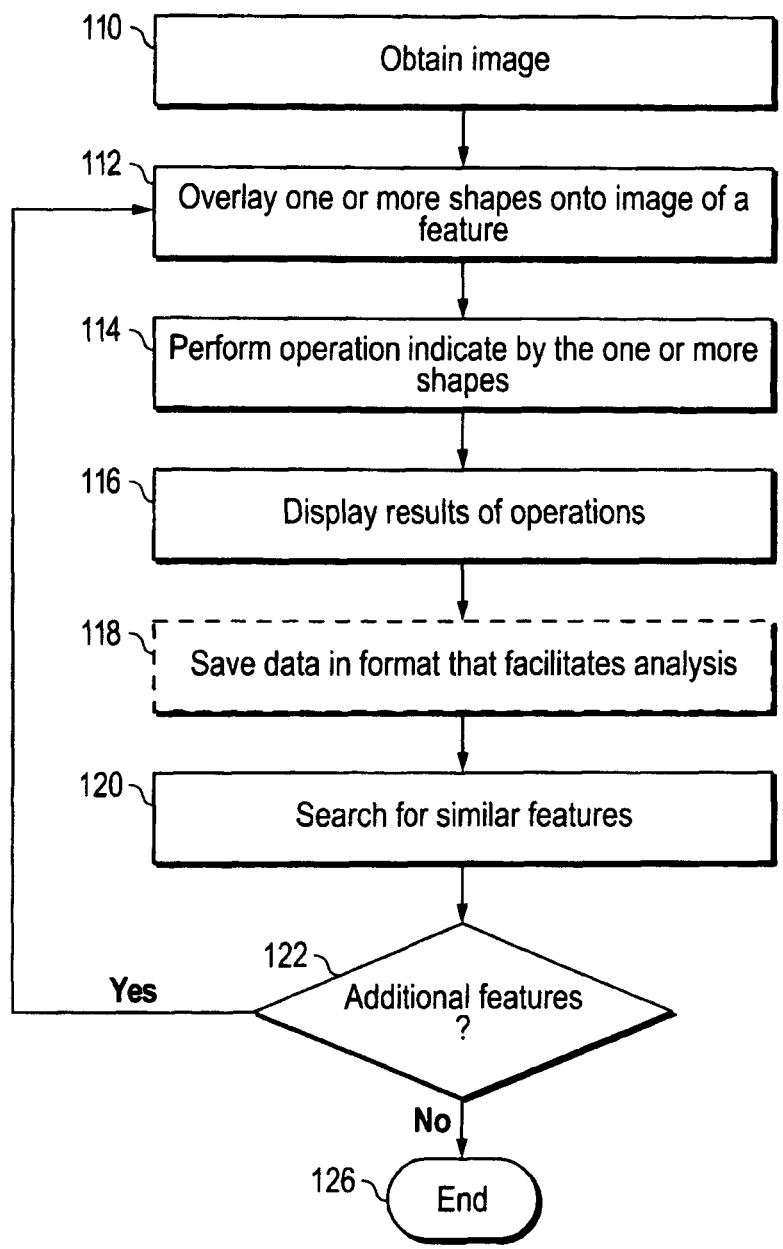
Figure 2A:
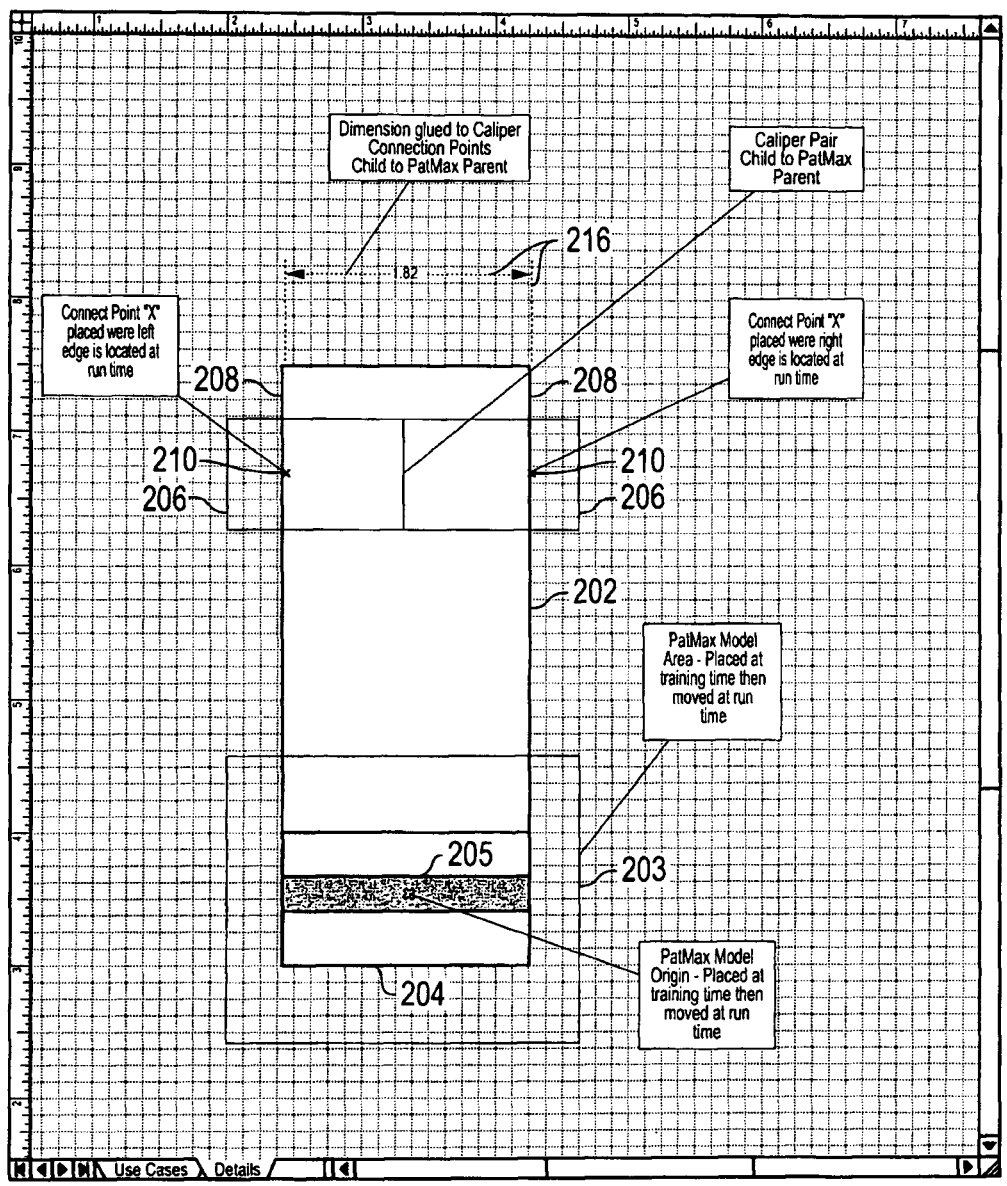
Figure 3:
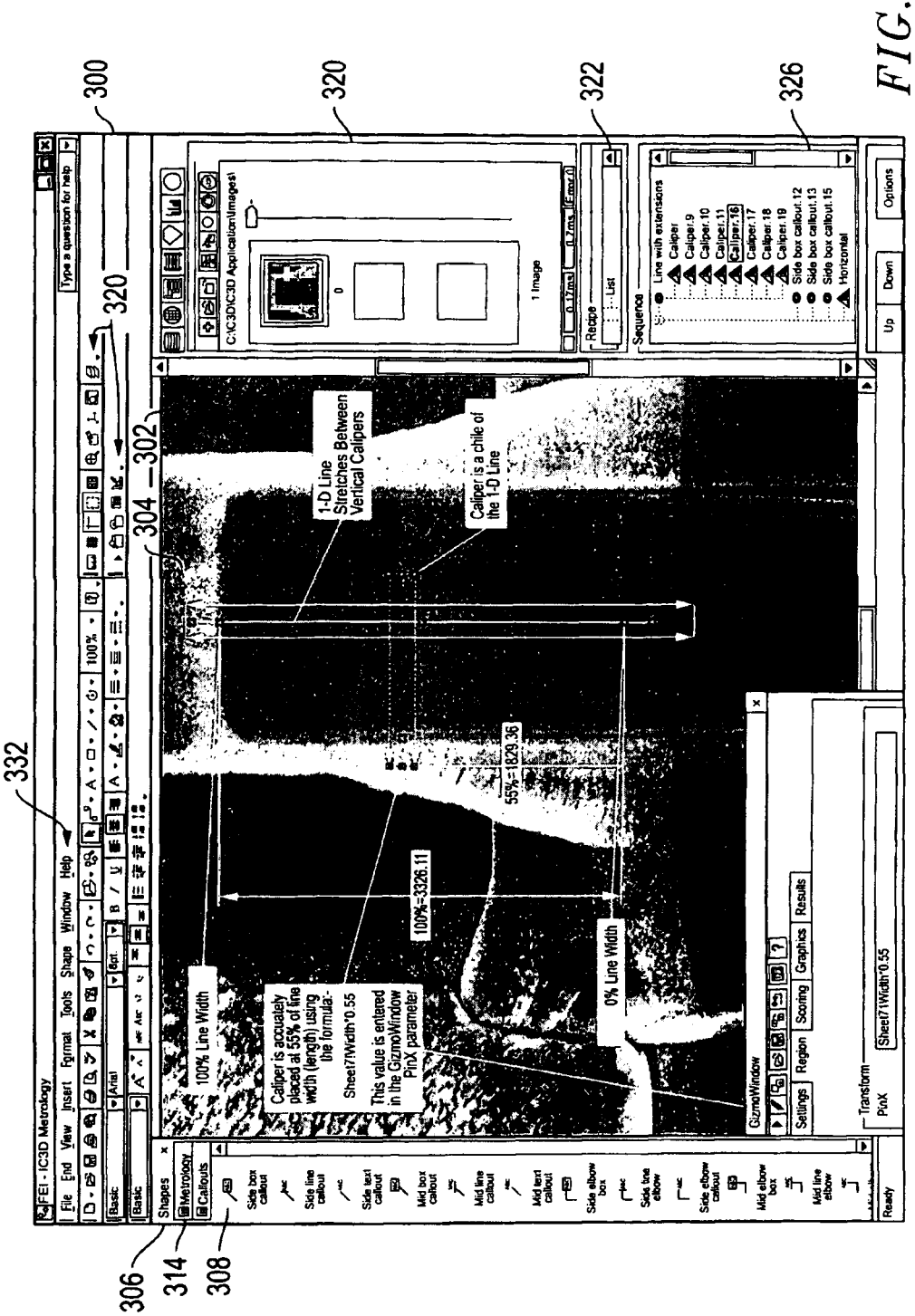
Figure 5:
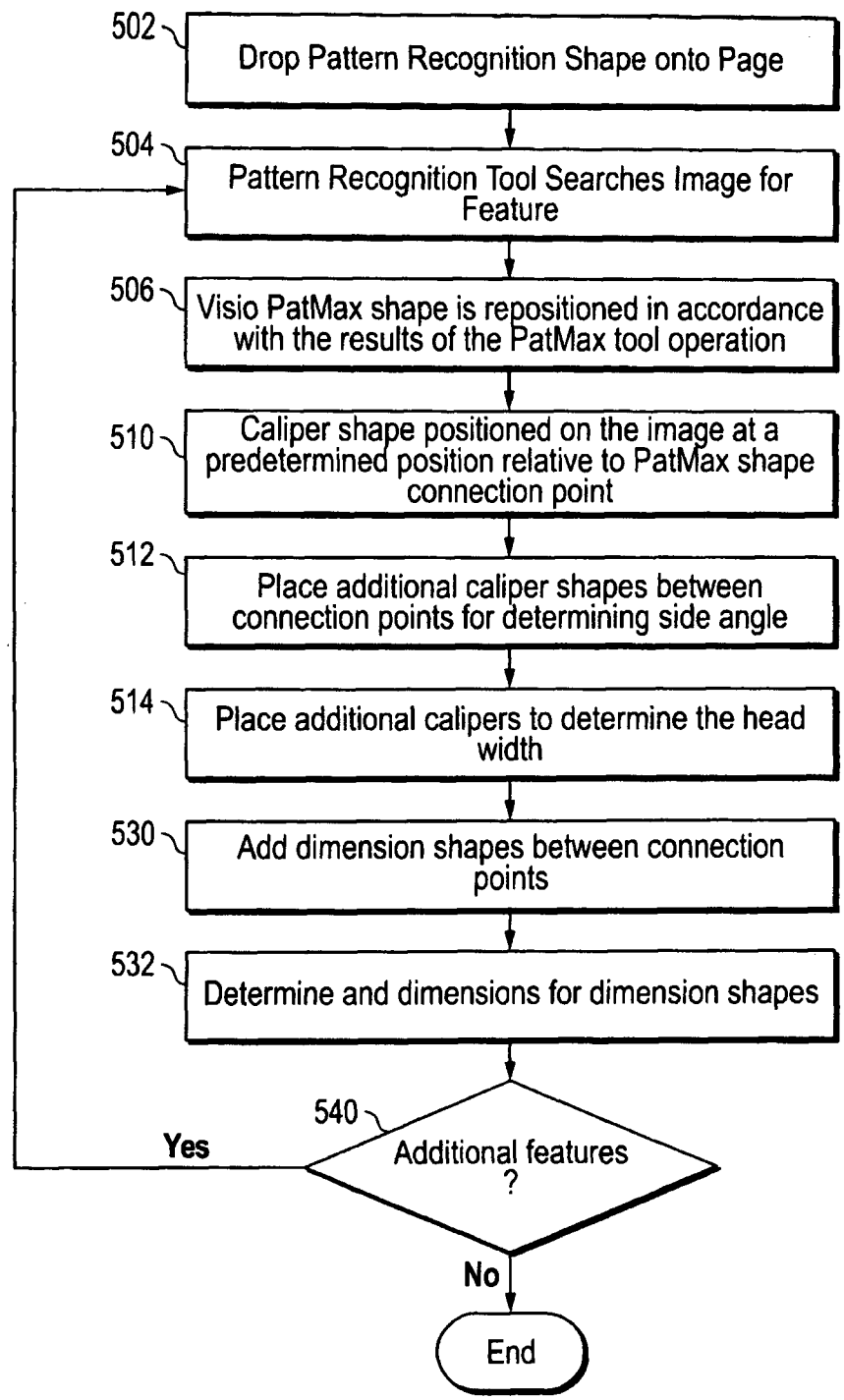
Figure 11:
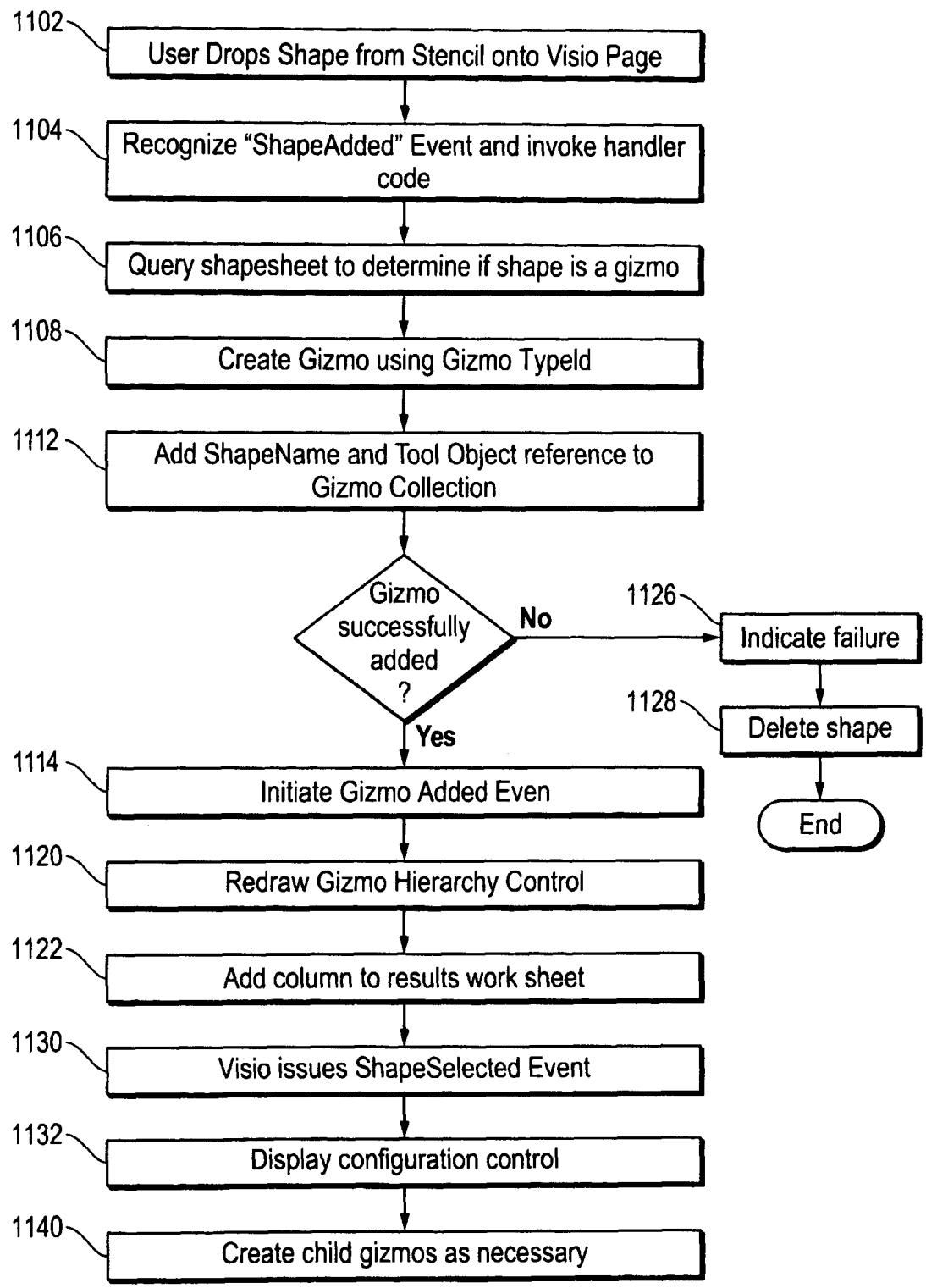

FIG. 13 shows an example of the use of a conditional branching. A TEM sample is coarsely milled in step 1302. The sample is measured in step 1304 and if the desired thickness is not reached, decision block 1306 indicate that milling continues with step 1302 until a desired thickness if reached. It is then finely milled in step 1310 and if the desired thickness is not reached, decision block 1312 indicate that fine milling continues with step 1310 until a desired thickness if reached. The sample is removed in step 1316. Based upon the description above regarding interfacing Visio with vision software and charged particle systems using VBA and active X, a skilled person could readily incorporate flow charting with conditional branching into the Visio pages described above. The VBA form data interacts with the shapes to provide the desired thickness and the actual thickness measurement. Visio allows placing window controls, such as button, onto a page to create a custom interface as shown FIG. 13. The custom interface displayed can be dependent upon the recipe that is chosen.

Different embodiments can operate in different modes. In a first mode, the invention can be used to automate a charged particle beam system. In this mode, the system controls every aspect of loading a wafer, navigating to sites on the wafer, preparing sites on the wafer and measuring features on the wafer. The invention can also be used in an offline mode. In this mode, the system is not connected to a microscope and can be executed on a laptop or desktop computer system. The user selects a number of images to measure from a database and sets the image scaling in terms of image pixels per nanometer, meter or kilometer and executes a metrology sequence on those images.

The invention is not limited to metrology, but can be used to graphically construct and execute a sequence to specify automatic control operations of any type, particularly image-based operations. Areas of application include but are not limited too:—

Automatic guidance of astronomical telescopes including object location, identification, and classification.
Automatic piloting of optical microscopes including feature location, identification, and classification.
Automated identification and quantification of DNA microarray spots.
Image based navigation of moving mechanical vehicles, robots or probes.
Image based computer numerical control (CNC) machine tool control and automation.
Lithography mask defect identification and repair or defect removal.
3-D nanofabrication and 3-D inspection.
Semiconductor defect identification, precision cross-sectioning and classification.
Thin film coating analysis.
Automated and manual image annotation.
Manufacturing line optical inspection and binning (dispositioning)

The user can program site sequences by combinations milling, imaging, moving, locating features and edges by dragging shapes off the stencil, and placing them on the page. A user can combine shapes and store the combination as a new Master on the stencil.

There is basically no limit to the combinations. The total configuration can include hundreds of shapes. The user only has to adjust the vision shape search areas, train PatMax tools and set caliper thresholds before the metrology is ready to be tested.

The invention allows control of multiple instruments, such the scanning electron microscope and the focused ion beam of a dual beam system, and could also control other instruments, such as an optical microscope.

Different embodiments of the invention allow automation of complex metrology operations without requiring the user to write any program code. Some embodiments allow a user to create sequences, hierarchies, and relationships graphically. The invention can operate on any kind of image from any source and allows scaling calibration and measurement with little or no specialized knowledge support from the system manufacturer. Providing a toolbox of specialized tools and a simple way to combine tools allows the user to program complex operations in a simple manner. Tool relationships such as fixturing allows a complete geometric description of target features. The invention can be readily adapted to new hardware by using a different machine communication library and new Gizmos.

The invention is broadly applicable to many types of systems and not all embodiments need incorporate all of the features or nor meet all of the objectives of the invention. The invention can be used to graphically specify any type of operations. The invention is not limited to charged particle beam systems. The invention is not limited to metrology, although it is particularly well suited to metrology operations. The invention is useful for control of machines, but it is not limited to control of machines, as indicated by the examples involving off-line image analysis.

Although the present invention and its advantages are described in detail above and below, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification.

As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

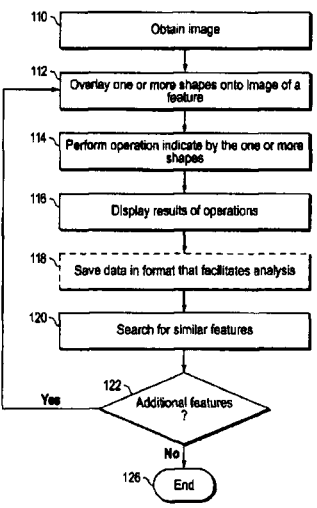

We claim:

1. A method of performing operations on an image or on an imaged object, comprising:

obtaining an image;

placing a first shape on the image, the first shape associated with executable pattern recognition computer instructions;

executing the executable pattern recognition computer instructions to locate a first feature;

repositioning the first shape to a location corresponding to the location of the first feature;

placing a second shape on the image, the position of the second shape being determined by the location of the first shape and the second shape being associated with second executable pattern recognition computer instructions;

executing the second executable pattern recognition computer instructions to locate a second feature;

placing a third shape on the image, the third shape specifying an operation the results of which are directly or indirectly dependent upon the positions of the first shape and the second shape.

2. The method of claim 1 in which placing a third shape on the image includes placing on to image a third shape that connects between the first shape and the second shape.

3. The method of claim 1 in which placing a third shape on the image includes placing on the image a third shape associated with computer instructions that measure a distance between the first shape and the second shape.

4. The method of claim 1 in which placing a third shape on the image includes placing on the image a third shape specifying an operation the results of which are indirectly dependent upon the positions of the first shape and the second shape through one or more intermediate shapes whose positions are ultimately dependent upon the positions of the first and second shape.

5. The method of claim 1 further comprising placing on the image one or more additional shapes, the positions of the one or more additional shapes depending upon the positions of the first shape and the second shape, and in which the results of the operation specified by the third shape are dependent upon the positions of the one or more additional shapes.

6. The method of claim 1 in which the operation specified by the third shape comprises a micromachining operation.

7. The method of claim 1 in which the operation specified by the third shape comprises a measurement operation.

8. The method of claim 1 in which executing the executable pattern recognition computer instructions associated with the second shape to locate a second feature includes locating an edge of a structure located by executing the executable pattern recognition computer instructions associated with the first shape.

9. The method of claim 8 in which placing a second shape on the image includes placing a second shape including fixture points for positioning additional shapes on the image.

* * * * *

UNITED STATES PATENT AND TRADEMARK OFFICE
CERTIFICATE OF CORRECTION

PATENT NO.      : 7,308,334 B2
APPLICATION NO. : 11/115751
DATED           : December 11, 2007
INVENTOR(S)     : David J. Tasker, Henri J. Lezec and David A. Head It is certified that error appears in the above-identified patent and that said Letters Patent is hereby corrected as shown below:

On the Title Page, please change "indicate" to read "indicated", see attached illustrative figure on the title page.

1. In the Drawings, Sheet 1, Figure 1, 114- please change "indicate" to read "indicated"; See attached 2. In the Drawings, Sheet 2, Figure 2A, 210- please change "placed were left" to read "placed where left"; See attached 3. In the Drawings, Sheet 2, Figure 2A, 210- please change "placed were right" to read "placed where right"; See attached 4. In the Drawings, Sheet 4, Figure 3, Top Left- please change "Caliper is accuately placed at 55% of line width" to read "Caliper is accurately placed at 55% of line width"; See attached 5. In the Drawings, Sheet 4, Figure 3, Center- please change "Caliper is a chile of the 1-D Line" to read "Caliper is a child of the 1-D Line"; See attached 6. In the Drawings, Sheet 6, Figure 5, 532- please change "Determine and dimensions" to read "Determine dimensions"; See attached 7. In the Drawings, Sheet 16, Figure 11, 1114- please change "Added Even" to read "Added Event"; See attached 8. Column 2, Line 63- please change "drawings" to read "drawing";

9. Column 6, Line 14- please change "embodiment is in" to read "embodiment in";

10. Column 6, Line 15- please change "obtain an images" to read "obtain images";

Signed and Sealed this
Fourteenth Day of June, 2011

David J. Kappos
*Director of the United States Patent and Trademark Office*

11. Column 6, Line 47- please change "manual" to read "manually";

12. Column 6, Line 60- please change "an computer" to read "a computer";

13. Column 7, Line 31- please change "as guide" to read "as a guide";

14. Column 11, Line 30- please change "can be each" to read "can each";

15. Column 11, Line 44- please change "dimensions" to read "dimension";

16. Column 12, Line 3- please change "Each of forms" to read "Each form";

17. Column 12, Line 62/63- please change "person" to read "persons";

18. Column 12, Line 63- please change "that the some" to read "that some";

19. Column 13, Line 45- please change "dimensions" to read "dimension";

20. Column 13, Line 49- please change "664" to read "666";

21. Column 15, Line 3- please change "place" to read "placed";

22. Column 15, Line 65- please change "devices" to read "device";

23. Column 16, Line 25- please change "simple" to read "simply";

24. Column 18, Line 14- please change "preferable" to read "preferably";

25. Column 18, Line 54- please change "-cogPersistOptionInput1mages" to read "-cogPersistOptionInputImages";

26. Column 18, Line 55- please change "-cogPersistOptionInputimages" to read "-cogPersistOptionInputImages";

27. Column 20, Line 10- please change "Tumed" to read "Turned";

28. Column 20, Line 16- please change "use" to read "uses";

29. Column 20, Line 30- please change "User.Gizmo1d Cell" to read "User.Gizmold Cell";

30. Column 20, Line 31- please change "Gizmoids" to read "Gizmolds";

31. Column 20, Line 32- please change "Progid's" to read "ProgId's";

CERTIFICATE OF CORRECTION (continued)
U.S. Pat. No. 7,308,334 B2

32. Column 20, Line 55- please change "1D" to read "ID";

33. Column 21, Line 5- please change "11 ML" to read "11ML";

34. Column 21, Line 36- please change "Gizmo manger" to read "GizmoManager";

35. Column 22, Line 42- please change "IDBTool.Output1mage.Width/2" to read "IDBTool.OutputImage.Width/2";

36. Column 22, Line 43- please change "IDBTool.Output1mage.Height/2" to read "IDBTool.OutputImage.Height/2";

37. Column 22, Line 46- please change "IDBTool.Output1mage" to read "IDBTool.OutputImage";

38. Column 22, Line 48- please change "IDBTool.Output1mage" to read "IDBTool.OutputImage";

39. Column 23, Line 19- please change "ControlProg1D" to read "ControlProgID";

40. Column 27, Line 31- please change "indicate" to read "indicates";

41. Column 27, Line 32/33- please change "if reached" to read "is reached";

42. Column 27, Line 34/35- please change "indicate" to read "indicates";

43. Column 27, Line 36- please change "if reached" to read "is reached";

44. Column 27, Line 44- please change "button" to read "buttons".

(12) United States Patent
Tasker et al.

(10) Patent No.: US 7,308,334 B2
(45) Date of Patent: *Dec. 11, 2007

(54) GRAPHICAL AUTOMATED MACHINE CONTROL AND METROLOGY

(75) Inventors: David J. Tasker, Hillsboro, OR (US); Henri J. Lezec, Strasbourg (FR); David A. Head, Hillsboro, OR (US)

(73) Assignee: FEI Company, Hillsboro, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 11/115,751

(22) Filed: Apr. 27, 2005

(65) Prior Publication Data

US 2005/0188309 A1 Aug. 25, 2005

Related U.S. Application Data

(63) Continuation of application No. 10/227,619, filed on Aug. 23, 2002, now Pat. No. 6,889,113.

(60) Provisional application No. 60/314,687, filed on Aug. 23, 2001.

(51) Int. Cl.
*G06F 19/00* (2006.01)
(52) U.S. Cl. .................... 700/180; 700/182
(58) Field of Classification Search .......... 700/180, 700/166, 182, 121
See application file for complete search history.

(56) References Cited

U.S. PATENT DOCUMENTS

| | | | |
|---|---|---|---|
| 3,877,019 A | 4/1975 | Auerbach et al. | |
| 5,163,006 A | 11/1992 | Deziel | |
| 5,815,154 A | 9/1998 | Hirschtick et al. | |
| 5,926,176 A | 7/1999 | McMillan et al. | |
| 5,970,243 A | 10/1999 | Klein et al. | |
| 6,058,333 A | 5/2000 | Klein et al. | |
| 6,064,386 A | 5/2000 | Felser et al. | |
| 6,065,858 A | 5/2000 | Yamaguchi et al. | |
| 6,118,448 A | 9/2000 | McMillan et al. | |
| 6,191,850 B1 | 2/2001 | Chiang | |
| 6,219,055 B1 | 4/2001 | Bhargava et al. | |
| 6,232,985 B1 | 5/2001 | Chase et al. | |
| 6,798,515 B1 | 9/2004 | Bachelder et al. | |
| 6,868,175 B1 * | 3/2005 | Yamamoto et al. | 382/145 |
| 6,889,113 B2 | 5/2005 | Tasker et al. | |
| 2002/0125905 A1* | 9/2002 | Borden et al. | 324/765 |
| 2003/0223066 A1 | 12/2003 | Lee et al. | |

* cited by examiner

*Primary Examiner*—Zoila Cabrera
(74) *Attorney, Agent, or Firm*—Scheinberg & Griner, LLP; Michael O. Scheinberg; David Griner

(57) ABSTRACT

A graphical programming system allows a user to place geometric shapes onto a scaled image, the shape having associated behavior that operates on the image or on the object of which the image is formed. In a preferred embodiment, the shapes are objects in the Visio program by Microsoft Corporation. The shapes are dragged from a stencil onto an image provided by ion beam or electron microscope image. The shape invokes software or hardware to locate and measure features on the image or to perform operations, such as ion beam milling, on the object that is imaged.

9 Claims, 18 Drawing Sheets